US008354530B2

(12) United States Patent
Zlicar

(10) Patent No.: US 8,354,530 B2
(45) Date of Patent: Jan. 15, 2013

(54) PROCESS FOR THE SYNTHESIS OF ROSUVASTATIN CALCIUM

(75) Inventor: Marko Zlicar, Celje (SI)

(73) Assignee: Lek Pharmaceuticals d. d, Ljubljana (SI)

( * ) Notice: Subject to any disclaimer, the term of this patent is extended or adjusted under 35 U.S.C. 154(b) by 837 days.

(21) Appl. No.: 11/997,070

(22) PCT Filed: Jul. 26, 2006

(86) PCT No.: PCT/EP2006/007388
§ 371 (c)(1),
(2), (4) Date: Jan. 28, 2008

(87) PCT Pub. No.: WO2007/017117
PCT Pub. Date: Feb. 15, 2007

(65) Prior Publication Data
US 2008/0255170 A1    Oct. 16, 2008

(30) Foreign Application Priority Data

Jul. 28, 2005 (SI) .................................. 200500220
Nov. 10, 2005 (SI) .................................. 200500311

(51) Int. Cl.
*C07D 239/42* (2006.01)

(52) U.S. Cl. ...................................... 544/243; 544/332

(58) Field of Classification Search ............... 544/243, 544/332, 322
See application file for complete search history.

(56) References Cited

U.S. PATENT DOCUMENTS

| 5,110,825 | A | 5/1992 | Ogata et al. | |
| 7,312,329 | B2 * | 12/2007 | Joshi et al. | 544/243 |

FOREIGN PATENT DOCUMENTS

| EP | 0114027 | 7/1984 |
| WO | 00/49014 | 8/2000 |
| WO | 03/070717 | 8/2003 |
| WO | 2004/080963 | 9/2004 |
| WO | 2005/054207 | 6/2005 |

OTHER PUBLICATIONS

International Preliminary Report on Patentability, Written Opinion of International Searching Authority, dated Jan. 29, 2008.*
Keck G.E. et al: "A useful new enantiomerically pure synthon from malic acid:chelation-controlled activation as a route to regioselectivity" Journal of Organic Chemistry, American Chemical Society, Washington, DC, US, vol. 56. No. 1, 1991, pp. 417-420.

* cited by examiner

*Primary Examiner* — Venkataraman Balasubramanian
(74) *Attorney, Agent, or Firm* — Luedeka Neely Group, P.C.

(57) ABSTRACT

Present invention represents process for the preparation of HMG-CoA reductase inhibitors, in particular rosuvastatin calcium introducing L-malic acid as the source of chirality for the side chain.

16 Claims, No Drawings

PROCESS FOR THE SYNTHESIS OF ROSUVASTATIN CALCIUM

This application is the National stage of International Application No. PCT/EP2006/007388, filed on Jul. 26, 2006, which claims benefit under U.S.C §119 to Slovenian patent application number P200500220 filed on Jul. 28, 2005, and Slovenian patent application number P200500311 filed on Nov. 10, 2005, the contents of which are incorporated herein by reference in their entireties.

FIELD OF THE INVENTION

The present invention relates to a process for the preparation of HMG-CoA reductase inhibitors, in particular rosuvastatin calcium, introducing L-malic acid as the source of chirality for the side chain.

BACKGROUND OF THE INVENTION

Rosuvastatin is one of HMG-CoA reductase inhibitors, administered as its calcium salt. HMG-CoA reductase inhibitors (also called statins) are optically active molecules containing chiral (3R,5S)-hept-6-enoic or -heptanoic acid moiety. They are used for manufacturing medicaments to treat hypercholesterolemia. HMG-CoA reductase inhibitors are also simvastatin, pravastatin, lovastatin, atorvastatin and fluvastatin. Their pharmaceutical activity may be related to their structure where said chiral hepanoic or heptenoic acid (or a salt, ester or lactone) is bound to a core (denoted Het), which may be a heterocycle, such as substituted pyridine, pyrimidine, pyrrole.

Several methods were developed to introduce chirality into molecules, such as for example using optically active 3-silyloxyglutaric acid monoalkyl esters (WO 03/087112), 1-cyano-2(S)-[(t-butyldimethylsilyl)oxy]-4-oxo-5-triphenylphosphoranylidene-pentane (WO 2004/052867) or 3(S)-hydroxy-γ-butyrolactone (EP 521471). These reagents are rather complex so there is a need for simpler i.e. cheaper chiral sources.

DISCLOSURE OF THE INVENTION

In a general aspect of the invention there is provided a process for preparation of HMG-CoA reductase inhibitors characterized in that the statin core moiety is consecutively coupled with chiral segment containing 4 carbon atoms ($C_4$ segment) and a segment containing 2 carbon atoms ($C_2$ segment). The $C_4$ segment will carry a protecting group $R_4$ which will be removed prior or after the coupling with $C_2$ segment. The double bond (denoted as a) in the obtained intermediate is (if needed) converted into single bond; the keto group is reduced and any remaining protecting groups are removed. The final substance is (if desired) converted into salt, lactone or ester and if needed enantiomerically resolved. A chiral segment containing 4 carbon atoms is in accordance with our invention prepared from L-malic acid or derivative thereof.

In general the process of our invention is presented in following Scheme:

Scheme 1

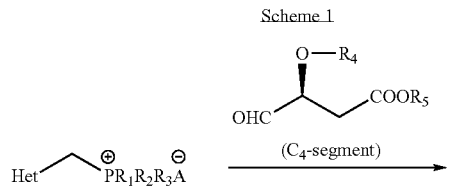

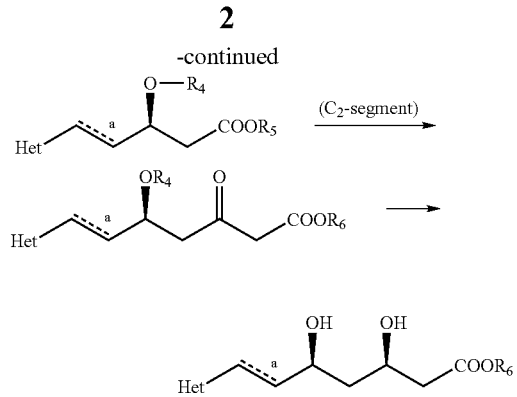

In this specification and in the Schemes a is a single or double bond;

$R_1$, $R_2$, $R_3$, $R_2'$, and $R_3'$ are the same or different and are selected from substituted or unsubstituted $C_1$-$C_{12}$ (preferably $C_1$-$C_8$, more preferably $C_1$-$C_4$)alkyl or $C_3$-$C_9$ (preferably $C_5$-$C_6$)cycloalkyl or $C_2$-$C_8$ alkenyl (preferably $C_2$-$C_5$) or $C_5$-$C_6$ cycloalkenyl or $C_5$-$C_{10}$ aryl, or heteroaryl (which means that it preferably contains 4 to 9 carbon atoms and 1 to 4 hetero, preferably N or O, atoms) preferably alkyl or aryl, preferably selected from methyl, ethyl, propyl, more preferably phenyl, butyl;

$A^\ominus$ is an anion of a strong acid, which has preferably pKa below 4, more preferably below 1.0, preferably $A^\ominus$ is halide or more preferably an anion of strong organic acid, more preferably an anion of organic sulfonic acid, halogenated aliphatic or aromatic acid, yet more preferably mesilate, fluoroacetate and most preferably trifluoroacetate; A (or denoted X as a leaving group) may (when covalently bound) preferably denote also halo, sulfonyl, alkoxy, acyl, acyloxy; preferably mesyl, haloacetyl, haloacetyloxy more preferably fluoroacetyloxy and most preferably trifluoroacetyloxy ($CF_3COO$);

$R_4$ is a protecting group, preferably silyl or methyl substituted by one or more substituents selected from $C_1$-$C_{12}$ (preferably $C_1$-$C_8$, more preferably $C_1$-$C_4$)alkyl or $C_3$-$C_8$ (preferably $C_5$-$C_6$)cycloalkyl or $C_2$-$C_8$ alkenyl (preferably $C_2$-$C_5$) or $C_5$-$C_6$ cycloalkenyl or $C_5$-$C_{10}$ aryl, or heteroaryl, which may be same or different and may be optionally substituted; 2-oxacycloalkyl (preferably containing 3 to 6 carbon atoms), or acyl (acyl being —(O)CR where R is $C_{1-7}$alkyl), acyloxy (acyloxy being —OC(O)R where R is $C_{1-7}$alkyl);

$R_5$ is $C_1$-$C_{12}$ (preferably $C_1$-$C_8$, more preferably $C_1$-$C_4$) alkyl or $C_3$-$C_9$ (preferably $C_5$-$C_6$)cycloalkyl or $C_2$-$C_8$ alkenyl (preferably $C_2$-$C_5$) or $C_5$-$C_6$ cycloalkenyl or $C_5$-$C_{10}$ aryl, or heteroaryl, any of which may be optionally substituted by halo and/or alkyl and/or aryl; and Het is a statin core residue, preferably of any of formulae:

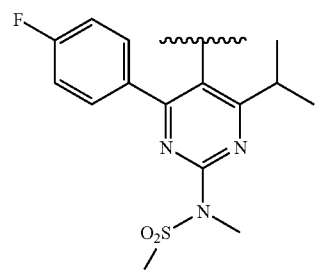

-continued

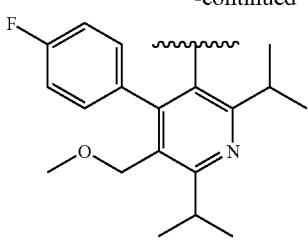

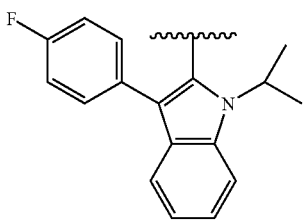

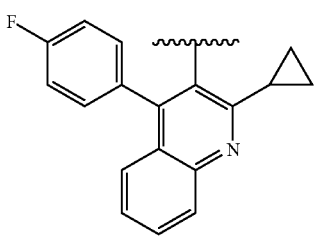

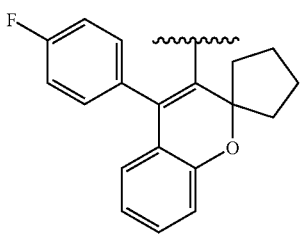

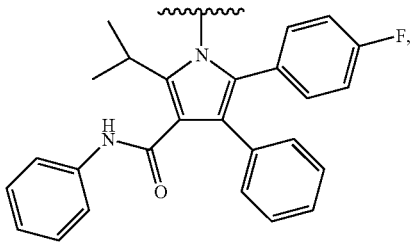

more preferably:

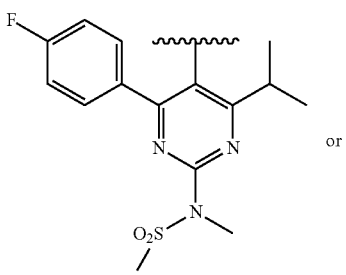

or

-continued

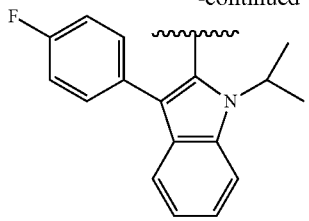

but also:

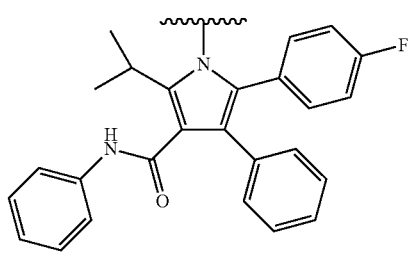

under certain conditions.
C$_2$ segment is selected from

MCH$_2$COOR$_6$,            Formula VIIa
⊕⊖

MCH$_2$CONR$_6$'R$_6$",  preferably     Formula VIIb
⊕⊖

CH$_3$COOR$_6$                    Formula VIIc

R$_6$ is preferably substituted (preferably by halo and/or alkyl (preferably C$_1$-C$_4$) and/or aryl (preferably C$_5$-C$_{10}$) and/or heteroaryl) C$_1$-C$_{12}$ (preferably C$_1$-C$_8$)alkyl or C$_3$-C$_8$ (preferably C$_5$-C$_6$)cycloalkyl or C$_2$-C$_{12}$ alkenyl (preferably C$_2$-C$_5$) or C$_5$-C$_6$ cycloalkenyl or C$_5$-C$_{10}$ aryl, or heteroaryl; preferably: C$_1$-C$_{12}$ alkyl or C$_2$-C$_{12}$ alkenyl, C$_3$-C$_8$ cycloalkyl or cycloalkenyl, optionally substituted by one or more alkyl, alkenyl, cycloalkyl, cycloalkenyl, (any of them having up to 6 carbon atoms), aryl (having 5 to 10 carbon atoms), which may themselves also be substituted. R$_6$ is most preferably menthyl, bornyl, norbornyl, yet more preferably dimethyl propyl, phenyl dimethyl ethyl, and methyl isopropyl cyclohexyl;
R$_6$' and R$_6$" may be same or different and may be selected from the same group as R$_6$, but may be also H, or R$_6$' and R$_6$" may together with N form a nitrogen containing heterocycle, and wherein M is chosen from: lithium, sodium, potassium, or alternatively magnesium or calcium.
R$_1$, R$_2$, R$_3$ are most preferably butyl;
R$_4$ is most preferably C$_1$-C$_8$ trialkylsilyl, C$_1$-C$_4$ dialkylphenylsilyl, C$_1$-C$_4$ alkyldiphenylsilyl, or 2-oxa-cyclo C$_4$-C$_5$ alkyl, more preferably t-butyldimethylsilyl or 2-tetrahydropyranyl;
R$_5$ is most preferably C$_1$-C$_6$ alkyl, more preferably methyl or ethyl; and
R$_6$ is preferably sterically hindered alkyl, such as branched alkyl (e.g. tert-butyl, tert-amyl), or cycloalkyl or aryl substituted iso-propyl or tert-butyl, most preferably 2-phenyl-1,1-dimethylethyl (abbreviated phenyl dimethyl ethyl).
The term substituted in this specification means that the group may bear one or more additional substituents, preferably selected from halo or alkyl (preferably C$_1$-C$_6$, more preferably C$_1$-C$_4$), alkenyl, cycloalkyl, cycloalkenyl (all preferably C$_5$-C$_7$), aryl (preferably C$_5$-C$_{10}$) and acyl (being —(O) CR where R is C$_{1-7}$alkyl), or acyloxy (being —OC(O)R where R is $C_{1-7}$alkyl), which may bear additional substituents, preferably selected from halo, nitro, alkyl, alkenyl, cycloalkyl, cycloalkenyl, and aryl.

The possible overall sequence of synthetic steps is as follows:

a) reacting a compound of following formula:

or optionally a compound of following formula:

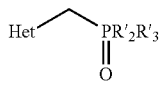

(under conditions of Wittig reaction) with a compound of Formula IV:

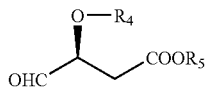

to prepare a compound of following formula:

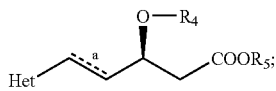

b) reacting the obtained compound with any of the compounds of following formulae:

to prepare a compound of following formula:

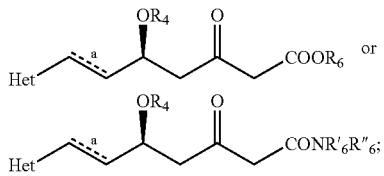

c) reacting the obtained compound with a stereoselective reducing agent
to prepare a compound of following formula:

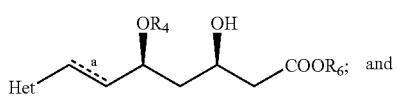

d) converting the obtained compound into acid, or salt thereof or lactone form; and in an appropriate step converting the $R_4$ protecting group into hydrogen;
and if needed in an appropriate step converting a, which denotes double bond into single bond.

The key portions of our synthesis are the process for preparation of compound of following formula:

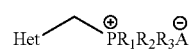

which comprises treating a compound of following formula:

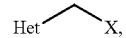

wherein X is a leaving group,
with phosphines of Formula X:

and
process for preparation of compound of following formula:

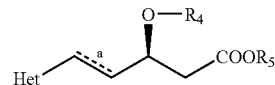

which comprises reacting a compound of following formula (phosphonium salt):

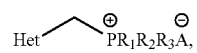

or optionally a compound of following formula (phosphonate):

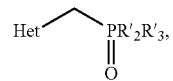

with a compound of Formula IV:

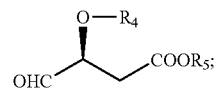

and
a process where the compound of following formula:

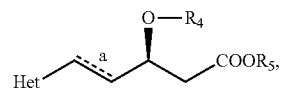

wherein $R_4$ is H or a protecting group,
is reacted with any of the compounds of following formulae:

and a process for preparation of compound of following formula:

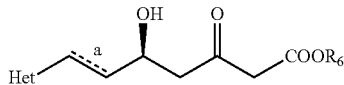

from compound of following formula:

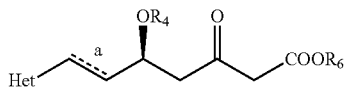

by treatment with a deprotecting agent, preferably fluoride; and a process for preparation of compound of following formula:

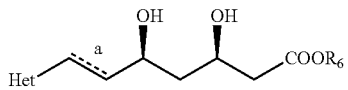

which comprises treating a compound of following formula:

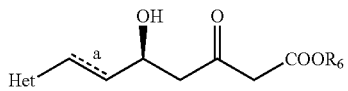

with a stereoselective reducing agent chosen from the group of borhydrides.

An aspect of the invention is also the formation of the following new compounds, which may be used as intermediates for manufacturing HMG-Co A reductase inhibitors, preferably for manufacturing rosuvastatin or alternatively fluvastatin:

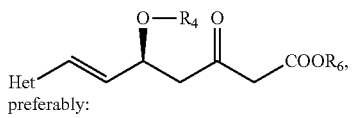

preferably:

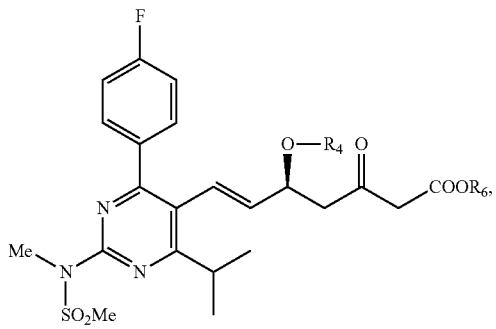

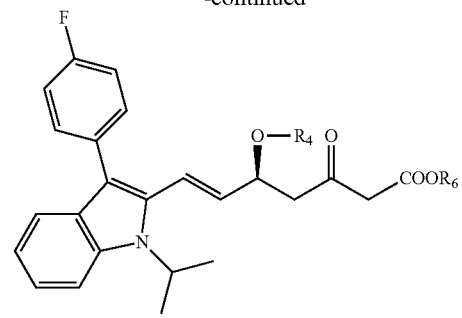

wherein, Het is as defined above, $R_4$ is t-butyldimethylsilyl, 2-tetrahydropyranyl or hydrogen, and $R_6$ is t-butyl, t-amyl, phenyl dimethyl ethyl, or methyl isopropyl cyclohexyl; preferably where $R_4$ is t-butyldimethylsilyl or hydrogen and $R_6$ is $C(CH_3)_2CH_2C_6H_5$ and compounds:

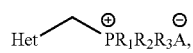

preferably of Formula III:

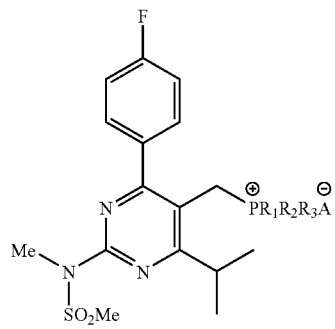

wherein Het is as defined above, A is trifluoracetate, fluoroacetate or mesylate and $R_1$, $R_2$, and $R_3$ are as defined above, preferably:
$R_1$, $R_2$, and $R_3$ are ethyl or $R_1$, $R_2$, and $R_3$ are n-butyl or $R_1$, $R_2$, and $R_3$ are methyl or $R_1$ and $R_2$ are phenyl, and $R_3$ is methyl or $R_1$ is phenyl, and $R_2$ and $R_3$ are methyl; more preferably where A is trifluoroacetate and $R_1$, $R_2$, and $R_3$ are n-butyl and their equivalent compounds of Formula IIIa:

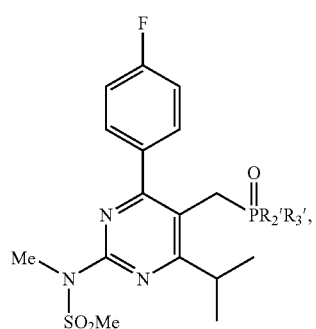

wherein $R_2'$, $R_3'$ are as defined above, preferably same or different selected from methyl, ethyl, propyl, butyl, phenyl.

The most characteristic reaction of the process is the Wittig reaction in which the first part of the side chain is constructed to the HMG-CoA reductase core. In one specific aspect the invention is a process for preparation of a compound (which is one of key intermediates):

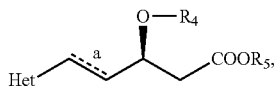

preferably of Formula V:

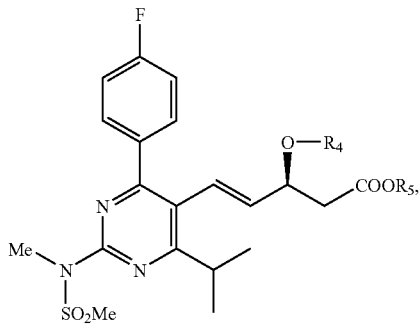

which comprises reacting a compound:

preferably of Formula III:

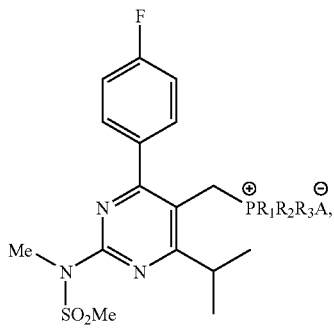

or optionally a compound:

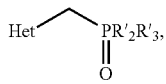

preferably of Formula IIIa:

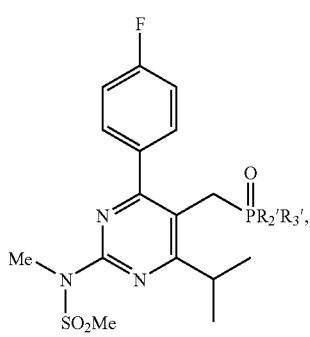

with a compound of Formula IV:

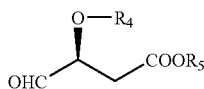

wherein Het, a, A, $R_1$, $R_2$, $R_3$, $R_2'$, $R_3'$, $R_4$, and $R_5$ are as defined above.

The process (Wittig reaction) is preferably performed in the presence of strong bases, preferably metal amides (preferably lithium diisopropylamide, optionally prepared in situ from alkyl lithium and the corresponding amine) or lithium hexamethyldisilazane, potassium hexamethyldisilazane or sodium hexamethyldisilazane (abbreviated HMDS) (which is most preferred).

The process is preferably performed at temperatures between $-70°$ C. and $40°$ C., preferably from $-45°$ C. to room temperature (RT), most preferably $-45$ to $-30°$ C., in an organic solvent or a mixture of organic solvents, preferably selected from ethers or aromatic hydrocarbons, more preferably tetrahydrofurane, or toluene, or a mixture of an aprotic organic solvent and tetrahydrofurane, or a mixture of an aprotic organic solvent and toluene.

In additional aspect the process as described above comprises following treatment of a reaction mixture steps: optionally concentrating a reaction mixture; acidifying a reaction mixture in the presence of water and extracting a product into water immiscible organic solvent; optionally washing an organic solvent solution of a product with water, water solution of an alkali salt or ammonium salt, and/or water solution of mineral acid; optionally washing an organic solvent solution of a product with a mixture water/polar organic solvent, preferably with water/dimethylsulphoxide mixture; optionally drying a solution with a drying agent; concentrating a solution to obtain residue, preferably by evaporation; optionally purifying a residue by column chromatography on silica.

Thus obtained compound may in an aspect undergo deprotection yielding compound:

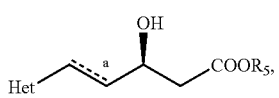

preferably of Formula VI:

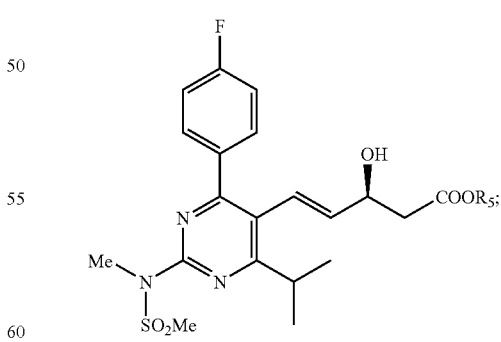

wherein Het, a and $R_5$ are as defined above. The deprotection is preferably done by fluoride for few hours at elevated temperatures, preferably 70-100° C. in a suitable solvent, such as acetic acid, followed by conventional work-up which may be extraction and/or chromatography and/or crystallization. There may be a subsequent reprotection step.

Our invention is characterized by the compounds thus obtained, in case a is double bond, preferably compounds:

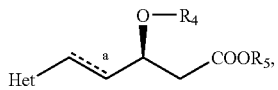

where Het, a, and $R_5$ are as defined above, and $R_4$ is H or protecting group, more preferably of Formula V, contains less than 4%, more preferably less than 1.0%, more preferably less than 0.5% and most preferably less than 0.2% of its Z-isomer. A subsequent aspect of our invention is a process, where compound:

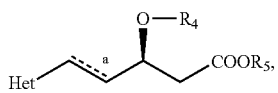

preferably of Formula V:

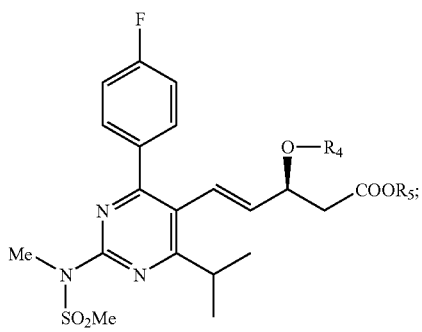

wherein $R_4$ is H, or protecting group as defined above, and Het and $R_5$ are as defined above is reacted with $C_2$ segment.

The process of this aspect is performed preferably in the presence of a strong base at temperatures between −80° C. and 0° C., preferably below −25° C. in an organic solvent or a mixture of organic solvents such as ethers or aromatic hydrocarbons or chlorinated hydrocarbons and is followed by acidification of the reaction mixture.

The $C_2$ segment being compound of Formula VIIIa:

is preferably prepared in situ from corresponding acetate, preferably $C_1$-$C_6$ alkyl acetate or $C_5$-$C_8$ cycloalkyl acetate, and alkali metal amide (preferably with lithium diisopropylamide, from branched alkyl, preferably (optionally substituted t-butyl acetate) in an organic solvent at temperatures between 0° C. and −80° C. Preferably the temperature is between −30° C. and −60° C. and an organic solvent is tetrahydrofuran (more preferred) or toluene. The preferred process of this aspect is where $C_2$ segment is compound of Formula VIIc:

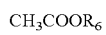

wherein $R_6$ is as defined above, preferably dimethyl propyl, phenyl dimethyl ethyl, and methyl isopropyl cyclohexyl.

The reaction is performed in the presence of strong bases, preferably lithium diisopropylamide, at temperatures between −80° C. and 0° C., preferably −75 to −45° C., more preferably −70 to −60° C., in an organic solvent or a mixture of organic solvents, preferably selected from ethers or aromatic hydrocarbons, most preferably tetrahydrofuran.

In a typical process, strong base is dissolved in solvent, and compounds of formula VIIc and phosphonium salt or phosphonate are added, while the temperature is maintained low and reaction mixture is stirred for few hours. Thereafter an acid, like acetic acid, is added and temperature is allowed to rise to RT, whereupon product is extracted and solvents evaporated.

Alternatively $C_2$ segment is compound of Formula VIIb:

where $R'_6$ and $R''_6$ are as defined above and thus produced product has in that case formula:

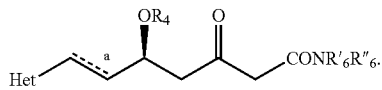

It is advantageous to use sterically hindered alkyl, such as branched alkyl, or cycloalkyl or aryl substituted iso-propyl or tert-butyl, preferably phenyl dimethyl ethyl as substituent $R_6$. Using hindered acetic esters prevents self-condensation of $C_2$ segments and favors the condensation with $C_4$ segment. Thus tertial alkyl esters are preferable compared to secondary and much preferable to primary alkyl esters. In the same condensation step in starting materials with free hydroxy groups (in formulae when $R_4$ is H) a side reaction of acetylation of the hydroxy group may further diminish the yield of the condensation step. In this case again sterically hindered esters are favorable and phenyl dimethyl ethyl ester is better than for example tert-butyl ester.

Subsequent aspect of the invention is a process for preparation of compound:

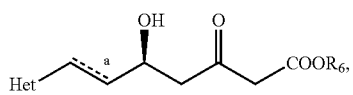

preferably of Formula VIII:

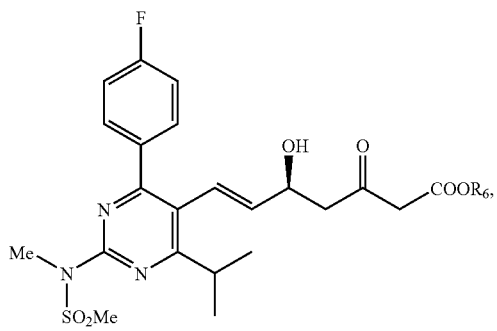

wherein $R_6$ is as defined above, from compound.

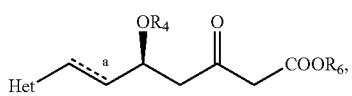

preferably of Formula XI:

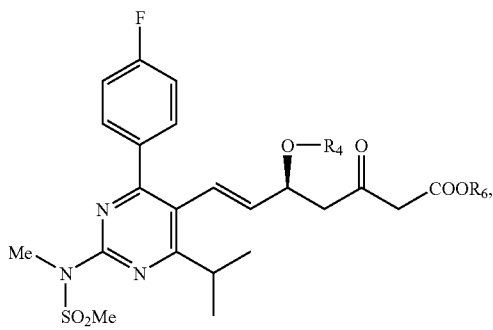

wherein $R_4$ is a protecting group as defined above, preferably $C_1$-$C_8$ trialkylsilyl, $C_1$-$C_4$ dialkylphenylsilyl, $C_1$-$C_4$ alkyldiphenylsilyl, or tetrahydropyranyl by treatment with a deprotective agent.

There is an advantage in using fluoride as deprotective agent because fluoride anion is a more efficient desilylating agent than oxygen or nitrogen nucleophiles, which could possibly also interact with other parts of HMG-CoA reductase skeleton. Preferably fluoride is made in situ by fluoride generating agents selected from ammonium fluoride, triethylamine trihydrofluoride or tetrabutylammonium fluoride. Deprotection is carried out in acidic medium preferably in acetic acid. Ammonium fluoride is preferred over conventionally used tetrabutyl ammonium fluoride, which is due to its solubility in organic solvents and surfactant properties harder to remove; ammonium fluoride is weaker, thus an alternative is triethylamine hydrofluoride. Alternatively to fluoride deprotection, 2-oxacycloalkyl protecting group is removed by use of sulfamic acid.

Specifically there is provided a process for preparation of compound of Formula XI, wherein $R_4$ is H and $R_6$ is as defined above, from compounds of Formula XI, wherein $R_4$ is 2-tetrahydropyranyl group deprotection is carried out in acidic medium, preferably in the presence of sulfamic acid. Additionally it is possible to prepare compound of Formula XI, wherein $R_4$ is different from H and $R_6$ is as defined above, from compound of Formula XI, wherein $R_4$ is H by the reprotection with protecting agent, preferably with diphenyldiazomethane if $R_4$ is diphenylmethyl or with 2,3-dihydropyrane if $R_4$ is tetrahydropyranyl.

Invention is in yet subsequent aspect a process for preparation of compound

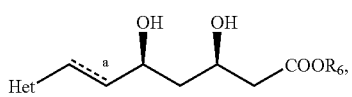

preferably of Formula IX:

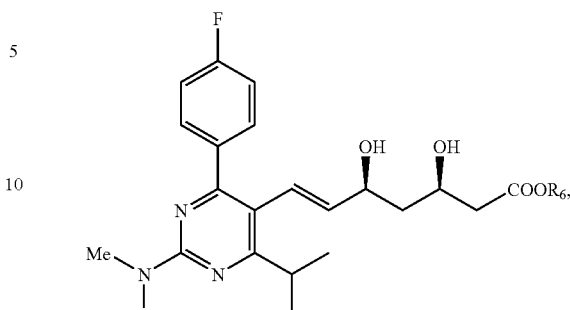

which comprises treating a compound

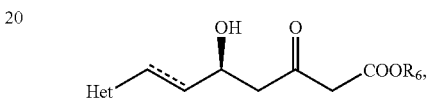

preferably of Formula VIII:

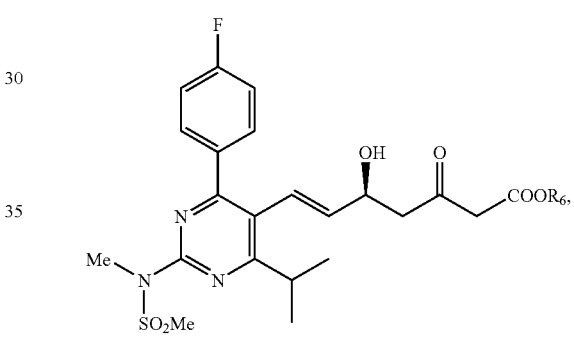

wherein $R_6$ is as defined above,
with a reducing agent chosen from the group of borhydrides. Reduction is preferably stereoselective and is carried out preferably by zinc borohydride or sodium borohydride in the presence of chelating agents, which promote selective reduction to cis-1,3-glycoles, such as di($C_1$-$C_4$)alkyl($C_1$-$C_4$)alkoxyboranes, preferably diethylmethoxyborane.

The reaction is performed at very low temperatures, preferably below −75° C., more preferably from −80--−100° C. and preferably under inert gas, preferably under nitrogen, in solvents such as ethers or aromatic hydrocarbons, preferably tetrahydrofuran in presence of small amount of an alcohol, preferably methanol. Reaction proceeds at very low temperature for a few hours, whereupon temperature may be allowed to rise to RT. An acid, such as acetic acid, is added and the product is isolated by evaporation of solvents. Thus produced compound is conveniently converted into an alkali, earth-alkali, ammonium, or amine salt by stirring with an alkali such as alkali or earth-alkali hydroxide, ammonia, an ammine and (if needed) subsequent transsalifying to yield desired salt of statin.

Aspect of the invention is also a process for preparation of compound:

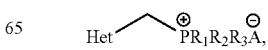

preferably of Formula III:

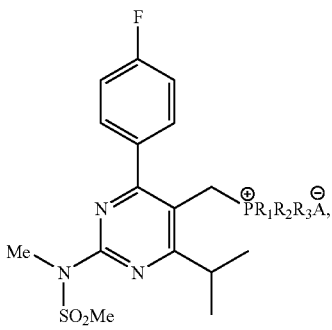

wherein $R_1$, $R_2$, $R_3$, and Het are as defined above, more preferably $R_1$ is $C_1$-$C_4$ alkyl, phenyl, $R_2$ is $C_1$-$C_4$ alkyl, phenyl and $R_3$ is $C_1$-$C_4$ alkyl, phenyl and A is as defined above, preferably halide, more preferably trifluoroacetate
which comprises treating a compound:

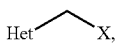

preferably of Formula II:

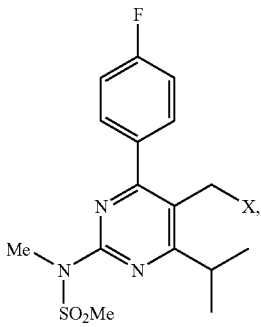

wherein X is leaving group, preferably halogen or more preferably an alkanoyloxy, arenecarboxy, alkanesulphonyloxy or arenesulphonyloxy, preferably alkanoyl ester of formula —CH$_2$OCOR wherein alkyl R (having 1 to 5 carbon atoms) is preferably halo substituted, more preferably trifluoroacetyl ester (of formula —O—C(O)CF$_3$),
with phosphines of Formula X

wherein $R_1$, $R_2$ and $R_3$ are as described above in a solvent or a mixture of solvents at temperatures between 0° C. and 80° C. Preferably the reaction is done in a solvent selected from THF or $C_1$-$C_4$ alkyl acetate or toluene or $C_1$-$C_4$ alcohol.

Specific aspect of our invention is a process for preparing a compound:

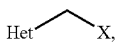

preferably of Formula II:

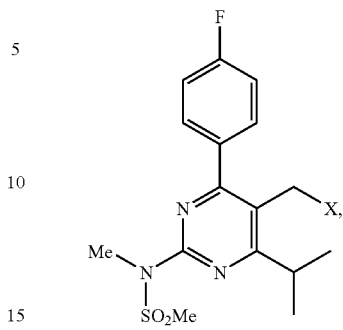

wherein X is halogen
which comprises halogenation of corresponding hydroxy compound (wherein X is OH), with phosphorous or sulphur halides or more preferably with an aqueous solution of concentrated hydrohalogenic acid at temperatures between 30° C. and 100° C. Preferably hydrohalogenic acid is aqueous solution of hydrobromic acid, which is preferably concentrated above at least 47%, more preferably at least above 62%.

Alternative specific aspect of our invention is a process for preparing a compound:

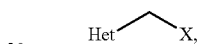

preferably of Formula II:

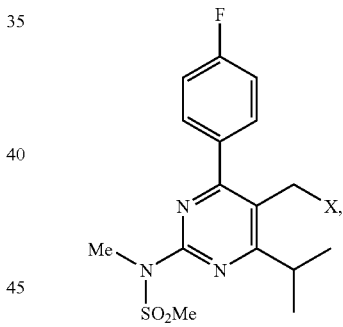

wherein X is ester as defined above, preferably halogenated alkanoyl or sulphonyl ester; which comprises esterification of corresponding hydroxy compound (wherein X is OH) with suitable acid or preferably its derivative, preferably acid halide or anhydride, most preferably with trifluoroacetic acid anhydride, in an aprotic solvent or mixture of solvents selected from ethers, esters, halogenated hydrocarbons, aromatic hydrocarbons and halogenated aromatic hydrocarbons, preferably dichloromethane, at temperatures between 30° C. and 150° C., more preferably around 100° C. or at the boiling point of the solvent. Specifically thus obtained compound may be directly used in subsequent reaction with phosphine without isolation or alternatively it is isolated and purified.

The convenient starting compound used for the manufacturing of HMG-CoA reductase inhibitors, preferably rosuvastatin or fluvastatin, in the synthesis process according to our invention is L-malic acid, and/or its derivative, preferably ester, more preferably dimethyl L-malate or diethyl L-malate.

The novel approach to synthesize HMG-CoA reductase inhibitors will now be described in detail. We have specifically exemplified the new synthetic approach towards (S—(R*, S*-(E)) 7-(4-(4-fluorophenyl)-6-(1-methylethyl)-2-(methyl(methylsulfonyl)amino)-5-pyrimdinyl)-3,5-dihydroxy 6-heptenoic acid (rosuvastatin), as an example of compounds where Het is a nitrogen containing six membered heterocycle. The procedures described here may be adapted to synthesize other structurally similar compounds.

An embodiment of the invention is a process for preparation of HMG-CoA reductase inhibitors characterized in that the statin core moiety is (using Wittig reaction) consecutively coupled with chiral segment containing 4 carbon atoms and a segment containing 2 carbon atoms and thus obtained compound is subsequently converted into HMG-CoA reductase inhibitor or its salt. Statin core moiety is methyl substituted by a statin core (denoted in this specification as Het) phosphonium salt or phosphonate:

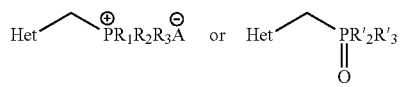

In one embodiment of the invention the complete syntheses is presented in Scheme 2 and in other embodiment in Scheme 3, where steps to compound Formula V may be the same as in Scheme 2. The alternative steps from compound Formula II to Formula V are presented in Scheme 4. In both embodiments a new pathway was introduced for the synthesis of HMG-CoA reductase inhibitors, particularly rosuvastatin by consecutive coupling of HMG-CoA reductase inhibitors core, particularly pyrimidine-$C_1$ rosuvastatin moiety of Formula III or alternatively Formula IIIa with chiral $C_4$ segment depicted by Formula IV and $C_2$ segment depicted by Formula VIIa to VIIc.

Alternatives to above aspects are also processes where instead of compound of Formula III in reaction with $C_4$ segment one uses the compound where Het is a nitrogen containing five membered heterocycle, preferably:

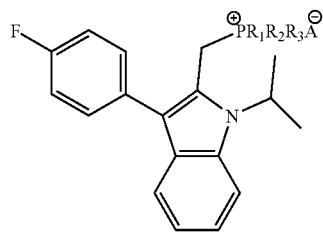

and its derivatives corresponding to Formulae VI, VII, IX, XI in subsequent reactions. An aspect of the invention is also a process, where the double bond, in compound obtained in Wittig reaction or in subsequent reactions, is hydrogenated, preferably using palladium or platinum catalyst.

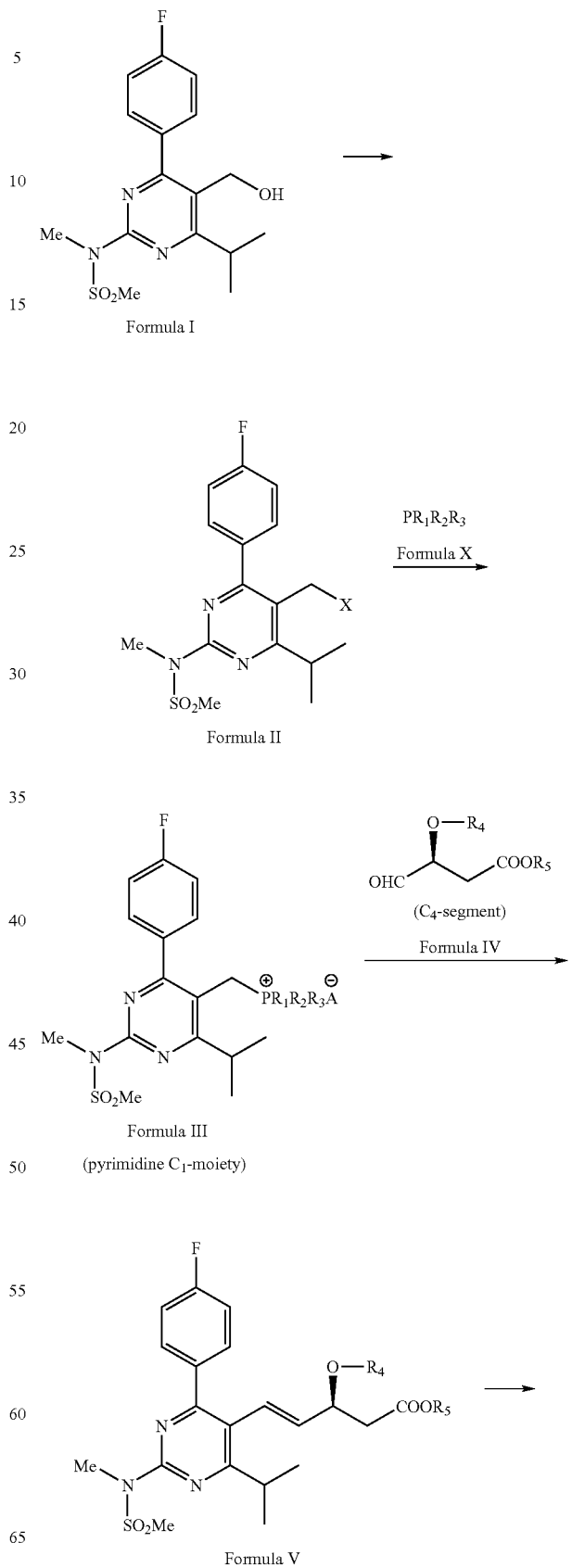

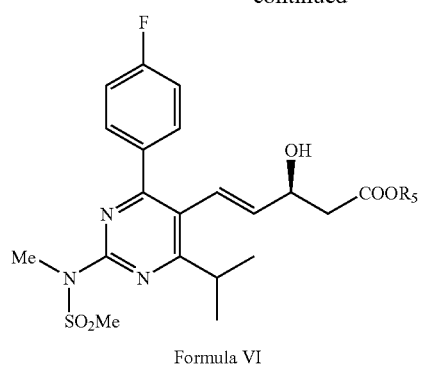
Formula VI
(C₂-segment)
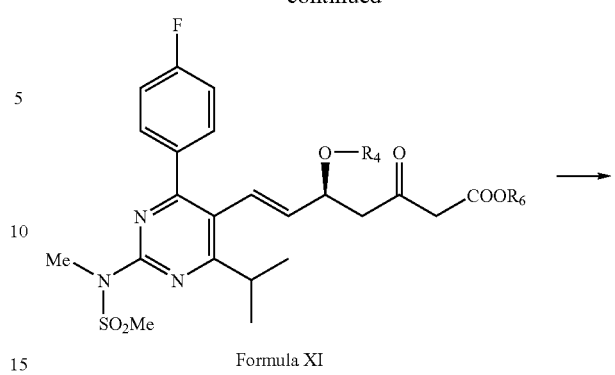
Formula XI
Formula VIII
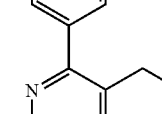
Formula VIII
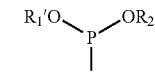
Formula IX
Formula IX
Scheme 3
Scheme 4
Formula V
C₂ segment
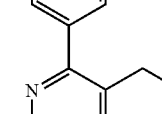
Formula II
Formula Xa -continued

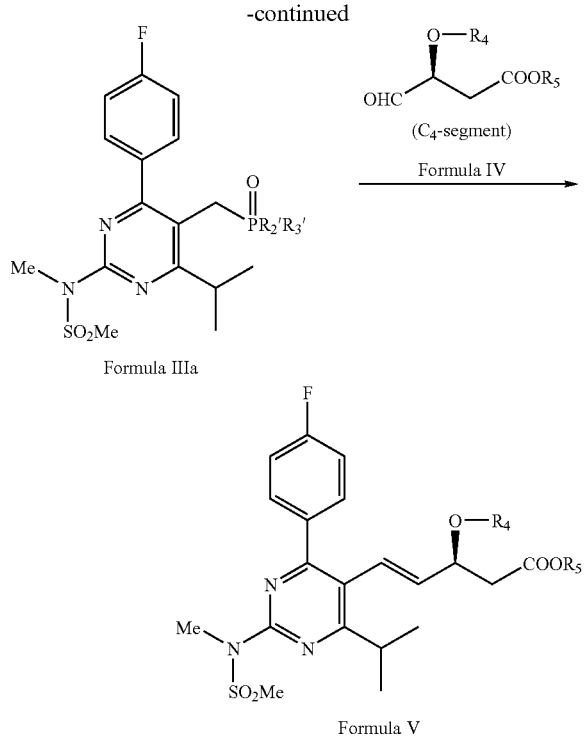

Formula IIIa

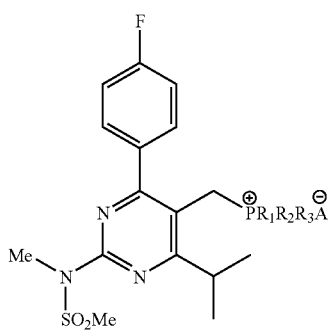

Formula V

In accordance with the invention, the compound of Formula III

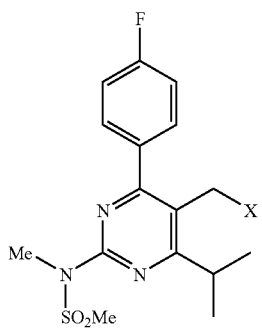

wherein $R_1$, $R_2$, and $R_3$ may be same or different and are selected from substituted or unsubstituted $C_1$-$C_8$ alkyl or $C_3$-$C_6$ cycloalkyl or $C_1$-$C_8$ alkenyl or $C_5$-$C_6$ cycloalkenyl or aryl, preferably $C_1$-$C_4$ alkyl, cyclohexyl, cyclopentyl or phenyl and $A^\ominus$ represents an anion as defined above, preferably trifluoroacetate may be prepared by treating a compound of Formula II

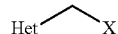

wherein X is a leaving group, such as halogen or ester, with phosphine of Formula X $PR_1R_2R_3$ wherein $R_1$, $R_2$ and $R_3$ are as defined above.

Preferably the reaction is performed at temperatures between 0° C. and 80° C., more preferably at about 50° C. preferably in a solvent or a mixture of solvents which are most preferably chosen from the group consisting of THF, $C_1$-$C_4$ alkyl acetate, toluene or $C_1$-$C_4$ alcohol.

It is known that carboxylic acid esters usually do not react with phosphines. Despite that we discovered that trifluoroacetyloxy derivative (Compound of Formula II where X is $OCOCF_3$) may be prepared in above 98% yield from hydroxyl derivative (Compound of Formula I) and that it subsequently reacts in 90% yield at 120° C. with tributylphosphine.

The compound of Formula III where $R_1$, $R_2$ and $R_3$ are butyl and A is trifluoroacetate is advantageous also in subsequent Wittig reaction. Contrary to bromide or mesylate salt it is well soluble in THF, it may be easily isolated in crystalline form as opposed to mesylate and only small optimizations are needed to attain yield of 90%, whereas the levels of side products are lower.

Compound of Formula III where $R_1$, $R_2$ and $R_3$ are phenyl and $A^\ominus$ is trifluoroacetate could be prepared from Compound of Formula II where X is $OCOCF_3$ in 88% yield. Similarly fluoroacetate may be prepared. Compounds of Formula II where X is $OCOCH_3$ or $OCOCH_2$—$C_5H_6$ are easy to prepare; however, they do not react with tributylphosphine in more than a few percent.

The phosphine of Formula X may be prepared according to known methods. The phosphine may be a mixed phosphine for example as prepared in J. Chem. Soc. Dalton trans., 1984, 293-295 or J. Org. Chem., 1995, 60, 5190-5208. It is advantageous to use tributylphosphine.

The above compounds of Formula II may be prepared by halogenation or esterification of a compound of Formula I (5-hydroxymethyl-4-(4-fluorophenyl)-6-isopropyl-2-[methyl(methylsulfonyl)amino]pyrimidine). The halogenation is preferably performed in a water solution of concentrated hydrohalogenic acid at temperatures between 30° C. and 100° C., more preferably at around 50-75° C. for up to a few hours. The esterification is preferably performed in an aprotic solvent or mixture of solvents selected from ethers, esters, halogenated hydrocarbons, aromatic hydrocarbons and halogenated aromatic hydrocarbons at low temperatures, preferably below 10° C., more preferably from −50 to 0° C. or at room temperature for up to few hours.

In the reaction proceeding from compound of Formula I to that of Formula III via ester, the ester of Formula II does not need to be isolated, in particular, when trifluoroacetic acid anhydride is used in first step and tributylphosphine in second step. Said esterification is advantageous also because the reaction is quicker than halogenation.

Preferably the reaction from a compound:

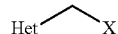

to compound

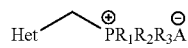

where Het, A, $R_1$, $R_2$, and $R_3$ are as defined above, with anion A, is carried out in a way that X is equal to A.

The invention is thus in specific embodiment a process for manufacturing a compound:

preferably of Formula III,
by reacting compound:

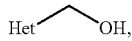

preferably of Formula I
first with trifluoroacetic acid or its derivative (preferably anhydride) and subsequently without isolation with triaryl phosphine (preferably triphenyl) or mixed alkyl aryl phosphine or more preferably trialkyl phosphine (most preferably tributyl).

Thus prepared compound is reacted with $C_4$ segment under conditions of Wittig reaction. The synthesis of $C_4$ segment is presented in Scheme 5.

Wittig reaction is known for creating molecules with a double bond. It is useful to have enough reactive and well defined phosphorous starting material which are selective enough for conversion into trans or cis derivatives. For particular compounds, phosphonium salts are more reactive than phosphonates. Furthermore we have surprisingly found that trialkylphosphonium salts are more selective in producing trans configuration (i.e. in any case less than 4%, in specific cases less than 1% of cis analogue, as conveniently determined by a suitable technique, e.g. HPLC or NMR) than more often used triphenyl analogues. Additionally it is desirable to avoid toxic waste and we have developed our specific Wittig reaction process with $C_4$ segment to avoid bromo compounds and aggressive reagents like often used phosphorous tribromide. Additionally, surprisingly phosphonium salts with some organic anions of our invention are very well defined, e.g. trialkylphosphonium salts are easier to crystallize compared to triphenyl analogues with greasy characteristics. Trifluoroacetates are the easiest to prepare and have the most favorable physicochemical properties.

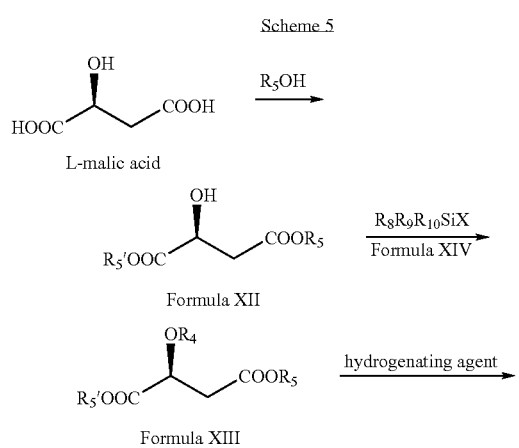

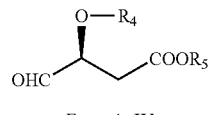

The compound of Formula IV (referred to as $C_4$ segment):

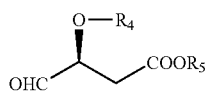

wherein $R_4$ is a protecting group as defined above, preferably a silyl or methyl substituted by one or more substituents selected from alkyl, cycloalkyl, alkenyl, cycloalkenyl, aryl which may be same or different and may be optionally substituted; or acyl protecting group, more preferably a silyl or methyl substituted by three same or different substituents selected from alkyl, cycloalkyl, alkenyl, cycloalkenyl, aryl, more preferably a protecting group selected from $C_1$-$C_8$ trialkylsilyl, $C_1$-$C_8$ dialkylphenylsilyl, $C_1$-$C_8$ alkyldiphenylsilyl or groups as above containing instead of silyl a methyl, such as: tert-butyldimethyl silyl, diphenylmethyl or trityl and $R_5$ is selected from $C_1$-$C_{12}$ alkyl, or alkenyl or $C_5$-$C_7$ cycloalkyl or alkenyl or aryl which may be optionally substituted, preferably $C_1$-$C_6$ alkyl, cyclopentyl or cyclohexyl, may be prepared by treating a compound of Formula XIII,

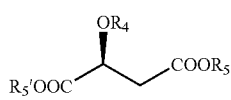

where $R_5$ may be the same or different as $R_5$ and if different $R_5$ may be selected from same groups as $R_5$;

with a reducing agent capable of converting COOR$_5$' into aldehyde in an organic solvent, optionally in the presence of carboxy ester complexing agent chosen from the group consisting of magnesium, calcium, lithium, zinc salts of strong inorganic acid in presence of magnesium bromide or magnesium etherate complex, in tetrahydrofurane, 1,2-dimethoxyethane, dichloromethane, toluene or diethyl ether as an organic solvent.

The reducing agent capable of converting COOR$_5$' into aldehyde may be selected from boron or aluminium hydrides preferably di-iso-butylaluminium hydride and reaction preferably takes place at low temperatures, preferably below −10° C., more preferably from −90 to −25° C., and is completed within a few minutes to a few hours. It is preferable that $R_5$' and $R_5$ are same, because the group closer to OR$_4$ will preferentially react with the reducing agent.

The workup may comprise following steps: washing a reaction mixture with Rochelle salts aqueous solution and/or optionally with water, or an aqueous alkali salt solution; concentrating organic phase from previous step to obtain residue; and optionally purifying a residue by column chromatography on silica.

The compound of Formula XIII where $R_4$ is a silyl protecting group may be prepared by treating a compound of Formula XII:

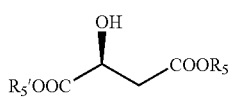

with a compound Formula XIV:

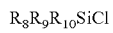

wherein $R_5'$ and $R_5$ are as defined above and $R_8$, $R_9$, and $R_{10}$ may be same or different and may be selected from substituted or unsubstituted preferably alkyl, cycloalkyl, alkenyl, cycloalkenyl, aryl, more preferably $C_1$-$C_8$ alkyl, $C_3$-$C_7$ cycloalkyl, and aryl, preferably $C_1$-$C_4$ alkyl, cyclohexyl, cyclopentyl, phenyl, preferably in a presence of an organic base in an aprotic organic solvent, preferably the solvent selected from mono-, di-, polyhalo $C_1$-$C_2$ alkane, N—($C_1$-$C_6$)alkyl imidazole, pyridine or substituted $C_1$-$C_2$ alkylpyridine, $C_1$-$C_6$ alkyl carboester, $C_1$-$C_4$ dialkyl ethers, tetrahydrofurane, N,N-dimethylformamide, N,N-dimethylacetamide, or mixture thereof at low or room temperatures, preferably between −10 and about 0° C. on ice bath for up to few hours. The product is conveniently isolated by concentrating reaction mixture, adding water and extracting into suitable solvent such as ether and evaporating said solvent.

The use of L-malic acid and its derivatives and preparation of already optically active $C_4$ segment as described above is advantageous, because desired stereochemistry is introduced into a complex molecule which does not need to be enantiomerically resolved, thus making process simpler and more economical, compared to those where separation is performed when the side chain is already attached to a HMG-CoA reductase core. The preparation of small $C_4$ segment with only one OH protecting group is also simpler than preparation of larger complete side chain, which would need to carry multiple or even multidental such protecting groups.

The compound:

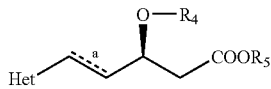

or if deprotection is done first:

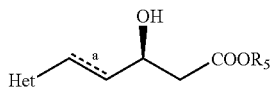

where Het, $R_4$ and $R_5$ are as defined above
is according to our invention subsequently coupled with $C_2$ segment. In the specific embodiment compound of Formula V or in alternative embodiment compound of Formula VI is reacted with any of the compounds of Formulas VIIa, VIIb, VIIc,

        Formula VIIa

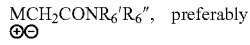 preferably        Formula VIIb

        Formula VIIc wherein M, $R_6$, $R_6'$ and $R_6''$ are as defined above.

Compound of Formula VIIb may be preferably N,N-dialkyl ($C_1$-$C_2$)—, N-alkyl($C_1$-$C_2$)—N-phenyl- and N,N-diphenylacetamide, and compounds of formula VIIa and VIIc may be preferably stericaly hindered esters, preferably dimethyl propyl acetate, methyl isopropyl cyclohexyl acetate and preferably phenyl dimethyl ethyl acetate (or in the case of VIIa their metal derivatives).

Reaction is performed preferably at temperatures between −80° C. and 0° C., preferably ethers or aromatic hydrocarbons, preferably tetrahydrofurane and if needed followed by acidification of the reaction mixture.

Before or after that reaction the protecting group $R_4$ as defined above may be removed as elaborated in Schemes. Thus in alternative specific embodiment related to rosuvastatin in schemes 2 and 3 reaction sequence proceeds through compounds of Formula VI or XI respectively, however in both cases at the end giving a compound of Formula VIII:

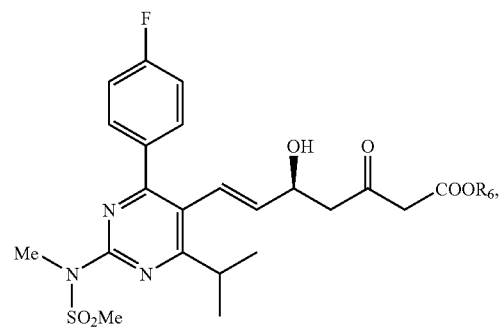

or in general:

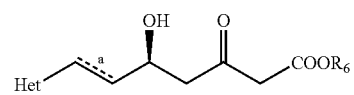

which may be with a stereoselective reducing agent chosen from borohydrides, such as combination of sodium borohydride with diethylmethoxy borane or zinc borohydride converted into an ester:

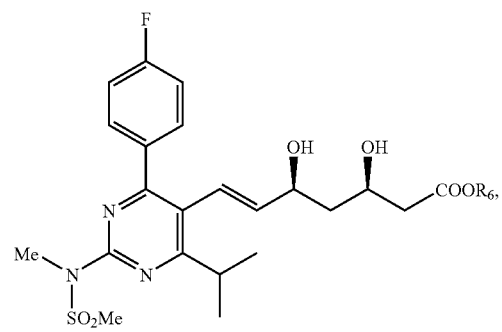

or in general:

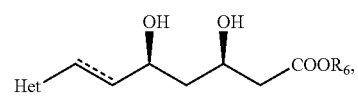

where $R_6$ is as described above, preferably $C_1$-$C_6$ alkyl, $C_5$ or $C_6$ cycloalkyl, bornyl, menthyl, more preferably dimethyl propyl acetate, methyl isopropyl cyclohexyl and most preferably phenyl dimethyl ethyl ester of Formula IX, where $R_6$ is $C(CH_3)_2CH_2C_5H_6$; which may be using the methods of prior art converted into rosuvastatin hemicalcium salt i.e. hydrolysis of the ester and conversion into calcium salt directly or via an intermediate such as other salt or lactone.

The stereoselective reducing agent is the reagent which will convert the compound possessing the oxy group into only one stereoisomer of hydroxy substituted compound (or protected hydroxy substituted compound) or into a mixture where the amount of one stereoisomer is higher than amount of the other.

The compound of Formula IIIa may be prepared from compound of Formula by reaction with compound of Formula Xa where $R_1$' may be same as any of $R_2$' and $R_3$' and may be selected from substituted or unsubstituted $C_1$-$C_8$ alkyl or $C_3$-$C_6$ cycloalkyl or $C_1$-$C_8$ alkenyl or $C_5$-$C_6$ cycloalkenyl or aryl, preferably $C_1$-$C_4$ alkyl, cyclohexyl, cyclopentyl or phenyl as depicted on Scheme 5.

The invention is illustrated with following nonlimiting working examples:

EXAMPLE 1

Dimethyl L-Malate

Compound of Formula XII, where $R_5$=$R_5$'=Me 100 g L-malic acid, 40 ml 37% HCl are heated in 700 ml methanol under reflux for 4 hours. The reaction mixture is concentrated under reduced pressure at 60° C. The residue is redissolved in 500 ml of methanol and concentrated again under reduced pressure. This redissolving and concentrating is repeated three times. After the last concentrating (final pressure is 10 mbars at 65° C.) 121 g of dimethyl L-malate remain in the flask. It is used in the next step without further purification.

EXAMPLE 2

Dimethyl O-t-butyldimethylsilyl-L-malate

Compound of Formula XIII, where $R_5$'=$R_5$=Me, $R_4$=t-butyldimethylsilyl

The mixture of 64.5 g dimethyl L-malate (compound of Example 1), 90 ml pyridine and 36 ml methylimidazole is being stirred on ice-bath, while 60.5 g t-butyldimethylsilyl chloride are added in two portions in 5-minute intervals. Stirring is continued for 1 hour on ice-bath and 3 hours at room temperature. Then, the reaction mixture is concentrated at 60° C. by evaporation at 60° C. and 20 mbars. After cooling to room temperature, 310 ml of demineralised water and 300 ml t-butyl methyl ether are added followed by the addition of 50 ml 45% phosphoric acid to reach a pH of the aqueous phase 2.5 which is separated and extracted again with 300 ml t-butyl methyl ether. Combined organic phases are washed consecutively with 1×250 ml of 4% phosphoric acid and 2×250 ml of demi water. The t-butyl methyl ether solution is finally dried with 75 g of anhydrous magnesium sulphate over 1 hour, followed by filtering off the drying agent and evaporating the resulting filtrate at 50° C. and 17 mbars to obtain 95.6 g of the clear liquid residue, which is used in the next step without further purification. $^1$H-NMR: (CDCl$_3$) 0.05 (3H, s), 0.09 (3H, s), 0.85-0.88 (9H, m), 2.68 (1H, dd), 2.79 (1H, dd), 3.67 (3H, s), 3.72 (3H, s), 4.62 (1H, dd)

EXAMPLE 3

Methyl 3 (S)-t-butyldimethylsilyloxy-4-oxo-butanoate

Compound of Formula IV, where $R_5$=Me, $R_4$=t-butyldimethylsilyl 40.0 g of dimethyl O-t-butyldimethylsilyl-L-malate (Compound of Example 2), 850 ml dichloromethane and 43 g magnesium bromide etherate (1:1) are stirred for 1 hour at room temperature under nitrogen. The mixture is cooled to −85° C. followed by the addition of 140 ml 1.2 M di-iso-butylaluminium hydride (DIBALH) in toluene diluted with 100 ml of dichloromethane over 1 hour. After the addition the reaction mixture is maintained for 1 hour at −80° C. and allowed to warm to −70° C. followed by the addition of 100 ml of methanol. Then the temperature is left to rise to −25° C. and the reaction mixture is poured into 1400 ml of a solution of Rochelle salts prepared from 65 g sodium potassium tartrate, 65 g sodium bicarbonate, 65 g sodium chloride and 1300 ml demi water. The resulting emulsion is stirred 2 hours at room temperature and left to rest forming two phases, which are separated. The aqueous phase is extracted with 300 ml dichloromethane. Combined organic phases are washed with 1×200 ml demi water and dried for 2 hours with anh. sodium sulphate. Evaporation of the organic phase at reduced pressure (15 mbars) and 60° C. results in 39.0 g of the clear liquid of crude methyl 3 (S)-t-butyldimethylsilyloxy-4-oxo-butanoate which is purified by chromatography: 39.0 g of the crude product are purified on 960 g of silica gel (particle size: 0.063-0.2 mm, height of the column: 60 cm, mobile phase: i-propyl acetate/dichloromethane=1:6) collecting the eluate at $R_f$=0.70. After the evaporation, 28.5 g of the product is obtained as a clear liquid. $^1$H-NMR: (CDCl$_3$) 0.03-0.09 (6H, m), 0.85-0.88 (9H, m), 2.58-2.80 (2H, m), 3.66 (3H, s), 4.34-4.38 (1H, ddm), 9.65 (1H, s).

EXAMPLE 4 p-methyldiphenylphosphine 37 ml p-chlorodiphenylphosphine are dissolved in 150 ml THF and during stirring on ice-bath 35 ml 3 M methylmagnesium bromide solution in diethyl ether is introduced gradually over 15 minutes. After addition of methylmagnesium bromide the reaction mixture is stirred an additional 15 minutes at room temperature. Thereafter 250 ml of i-propyl acetate are poured into reaction mixture followed by additional stirring for 5 minutes. The reaction mixture is washed consecutively with 100 ml demi water and 100 ml of 2% aqueous solution of ammonium chloride. The organic phase is evaporated under reduced pressure (final pressure: 12 mbars, 80° C.) and at elevated temperature (final pressure: 12 mbars, 80° C.) to give 40.0 g of oily residue of the product.

EXAMPLE 5

5-bromomethyl-4-(4-fluorophenyl)-6-isopropyl-2-[methyl(methylsulfonyl)amino]pyrimidine Compound of Formula II, where X=Br 50 g 5-hydroxymethyl-4-(4-fluorophenyl)-6-isopropyl-2-[methyl(methylsulfonyl)amino]pyrimidine (Compound of Formula I) and 100 ml 62% aq. HBr are stirred for 4 hours at 60-65° C. The solution formed is cooled to room temperature and poured into the mixture of 500 ml toluene and the solution prepared from 100 g tribasic potassium phosphate monohydrate in 500 ml water. All that time, the mixture is vigorously stirred at 0° C. After neutralization the stirring is continued for 15 minutes. Then the two layers are separated and aqueous phase is re-extracted with 150 ml of toluene and combined toluene phases are washed with 200 ml water. Toluene phase is evaporated under reduced pressure at 60° C. to dryness yielding 59.1 g of the yellowish solid product, which is used without purification in the next step.

EXAMPLE 6

({4-(4-fluorophenyl)-6-isopropyl-2-[methyl(methylsulfonyl)amino]-5-pyrimidinyl}methyl)(methyldiphenyl)phosphonium Bromide Compound of Formula III, where $R_1=R_2=Ph$, $R_3=Me$, X=Br 30 g 5-bromomethyl-4-(4-fluorophenyl)-6-isopropyl-2-[methyl(methylsulfonyl)amino]pyrimidine (Compound of Example 5) and 19 ml methyldiphenyphosphine in 120 ml THF are stirred for 15 minutes at 50° C. forming dense suspension. The reaction mixture is cooled to room temperature following the addition of 120 ml of diethyl ether. Stirring is continued for 1 hour on ice-bath whereupon the product is filtered off, washed on the filter with 70 ml of diethyl ether and dried in vacuum desiccator at 60° C. for 6 hours.

Yield: 45.2 g.

Analogously, triethyl-, trimethyl-, tributyl-, dimethylphenyl- and triphenylphosphonium bromides are prepared as follows: 1.0 g 5-bromomethyl-4-(4-fluorophenyl)-6-isopropyl-2-[methyl(methylsulfonyl)amino]-pyrimidine is suspended in 5 ml THF. 1.1 equivalent (1.2 equivalents of trimethylphosphine or triethylphosphine are used due to their volatility) of the corresponding phosphine is added. The reaction mixture is stirred 30 minutes at 50° C. Then it is cooled to RT following the addition of 5 ml of diethyl ether and stirring is continued 30 minutes on ice-bath. The product is filtered off, washed with 5 ml diethyl ether and dried. Yields: dimethylphenylphosphonium salt (97%), methyldiphenylphosphonium salt (98%), tributylphosphonium salt (85%), triethylphosphonium salt (92%), trimethylphosphonium salt (89%).

EXAMPLE 7

Di-i-propyl({4-(4-fluorophenyl)-6-isopropyl-2-[methyl(methylsulfonyl)amino]-5-pyrimidinyl}methylphosphonate (Compound of Formula IIIa, where $R_1=R_2$=i-propyl)

9.5 g 5-bromomethyl-4-(4-fluorophenyl)-6-isopropyl-2-[methyl(methylsulfonyl)amino]-pyrimidine (Compound of Example 5), 8.4 ml tri-1-propyl phosphate in 72 ml toluene are stirred for 17 hours at 90° C. Thereafter the reaction mixture is cooled to room temperature and washed with 3×80 ml of demi water. Volatile materials of the organic phase are distilled off at 60° C. and 25 mbars. The syrupy residue is purified by column chromatography on silica (630 g of silica 0.063-0.20 mm, mobile phase: dichloromethane/ethyl acetate=1:1, height=43 cm) collecting the fraction at Rf=0.52. The corresponding fraction is evaporated at 55° C. under reduced pressure (20 mbars). The oily residue crystallizes at cooling to room temperature and it is dried in vacuum desiccator at 50° C. 12 hours yielding 9.86 g of the product. $^1$H-NMR: (CDCl$_3$) 1.08 (6H, d), 1.19 (6H, d), 1.24 (6H, d), 3.14 (1H, s), 3.21 (1H, s), 3.42 (3H, s), 3.53 (1H, hept), 4.52 (1H, hept), 4.53 (1H, hept), 7.05-7.12 (2H, m), 7.60-7.67 (2H, m); MS: (EI) m/e, (%): 502(5), 460(15), 418(100), 400(7).

EXAMPLE 8

Methyl 5-(4-(4-fluorophenyl)-6-isopropyl-2-[methyl(methylsulfonyl)amino]pyrimidine-5-yl)-3(S)-t-butyldimethylsilyloxy-pent-4(E)-enoate Compound of Formula V, where $R_5$=Me, $R_4$=t-butyldimethylsilyl 25.0 g ({4-(4-fluorophenyl)-6-isopropyl-2-[methyl(methylsulfonyl)amino]-5-pyrimidinyl}methyl)(methyldiphenyl)phosphonium bromide (Compound of Example 6) is stirred in 160 ml THF. Thereto 24 ml 2M NaHMDS solution in THF is added at −30° C. gradually within 5 min under nitrogen. Stirring is continued for 20 minutes. Then, the temperature is lowered to 45° C. followed by the gradual addition of 16 ml methyl 3S-t-butyldimethylsilyloxy-4-oxo-butanoate (Compound of Example 3) within a 15-minute period. Resulting mixture is stirred 30 minutes at −45° C. Then, the temperature is elevated to −15° C. followed by the addition of 200 ml of hexane and 15 g 85% phosphoric acid in 100 ml demi water during continuous stirring. The resulting two-phase system is separated in a separatory funnel and organic phase is washed with 2×50 ml 77% vol DMSO/water and 2×100 ml 2% NaCl. Organic phase is evaporated under reduced pressure at 60° C. yielding 26.6 g of the crude product, which is used in the next step without purification.

EXAMPLE 9

Methyl 5-(4-(4-fluorophenyl)-6-isopropyl-2-[methyl(methylsulfonyl)amino]pyrimidine-5-yl)-3(S)-hydroxy-pent-4(E)-enoate Compound of Formula VI, where $R_5$=Me 26.6 g Methyl 5-(4-(4-fluorophenyl)-6-isopropyl-2-[methyl(methylsulfonyl)amino]pyrimidine-5-yl)-3(S)-t-butyldimethylsilyloxy-pent-4(E)-enoate (Compound of Example 8) and 8.6 g ammonium fluoride in 120 ml acetic acid are stirred for 2.5 hours at 77-80° C. under nitrogen. The reaction mixture is cooled to RT. 180 ml of demi water and 120 ml of toluene are added and the product is extracted into organic phase. Water phase is extracted again with 2×60 ml toluene. Combined toluene extracts are washed with 150 ml demi water containing 9 g K$_3$PO$_4$ monohydrate and 2×100 ml demi water. The organic phase is then evaporated at reduced pressure at 70° C. yielding 18.0 g of the product as the light-brown syrup. HPLC analysis showed that around 99.5% of product is in E-configuration.

Column Chromatography:

10.0 g of the crude product is purified on 510 g silica gel (particle size: 0.063-0.2 mm, height of the column: 55 cm, mobile phase: ethyl acetate/n-hexane=3:4) collecting the eluate at $R_f$=0.27. After the evaporation, 6.3 g off-white product are collected.

$^1$H-NMR: (CDCl$_3$) 1.27 (6H, d), 2.41 (1H, dd), 2.50 (1H, dd), 3.11 (1H, d), 3.35 (1H, hept), 3.52 (3H, s), 3.58 (3H, s), 3.72 (3H, s), 4.54-4.63 (1H, m), 5.49 (1H, dd, $J_1$=16 Hz), 6.68 (1H, dd, $J_1$=16 Hz), 7.05-7.16 (2H, m), 7.60-7.70 (2H, m)
MS: (EI) m/e, (%): 452(100), 346(10), 328 (14).

EXAMPLE 10 t-Butyl 7-(4-(4-fluorophenyl)-6-isopropyl-2-[methyl (methylsulfonyl)amino]pyrimidine-5-yl)-5(S)-t-butyldimethylsilyloxy-3-oxo-hept-6 (E)-enoate Compound of Formula XI, where
$R_4$=t-butyldimethylsilyl, $R_6$=t-butyl The solution of 4.8 ml 1.5 M lithium di-iso-propylamide (LDA) in cyclohexane is cooled to −45° C. and during stirring gradual addition of 0.9 ml t-butyl acetate follows maintaining the temperature of the reaction mixture at 45° C. Stirring is continued for 10 minutes, then 1.0 g methyl 5-(4-(4-fluorophenyl)-6-isopropyl-2-[methyl(methylsulfonyl)amino]pyrimidine-5-yl)-3 (S)-t-butyldimethylsilyloxy-pent-4 (E)-enoate (Compound of Example 8) is added. Stirring is continued for 20 minutes and the reaction mixture is poured into 20 ml 5% phosphoric acid. 10 ml of t-butyl methyl ether are added and the product is extracted into organic phase which is washed with 2×10 ml demi water. The solvents of the organic phase are evaporated off at reduced pressure at 60° C. 1.05 g of the of the light-brown syrupy mass of t-butyl 7-(4-(4-fluorophenyl)-6-isopropyl-2-[methyl(methylsulfonyl) amino]pyrimidine-5-yl)-5(S)-t-butyldimethylsilyloxy-3-oxo-hept-6(E)-enoate is used without purification in the next step.

EXAMPLE 11 t-Butyl 7-(4-(4-fluorophenyl)-6-isopropyl-2-[methyl (methylsulfonyl)amino]pyrimidine-5-yl)-5(S)-hydroxy-3-oxo-hept-6(E)-enoate Compound of Formula VIII, where $R_6$=t-butyl 1.0 t-Butyl 7-(4-(4-fluorophenyl)-6-isopropyl-2-[methyl (methylsulfonyl)amino]pyrimidine-5-yl)-5(S)-t-butyldimethylsilyloxy-3-oxo-hept-6(E)-enoate (Compound of Example 10) and 0.45 g ammonium fluoride in 6.0 ml acetic acid are stirred for 5 hours at 60-65° C. under nitrogen. The reaction mixture is cooled to RT. 10 ml of demi water and 10 ml of toluene are added and the product is extracted into organic phase. Water phase is extracted again with 2×5 ml of toluene. Combined toluene extracts are washed with 5 ml demi water containing 0.4 g $K_3PO_4$ monohydrate and 2×5 ml of demi water. The organic phase is then evaporated at reduced pressure at 70° C. yielding 0.85 g of the product as the light-brown syrup.

EXAMPLE 12 t-Butyl 7-(4-(4-fluorophenyl)-6-isopropyl-2-[methyl (methylsulfonyl)amino]pyrimidine-5-yl)-5(S)-hydroxy-3-oxo-hept-6(E)-enoate Compound of Formula VIII, where $R_6$=t-butyl The solution of 4.5 ml 1.5 M LDA in cyclohexane is cooled to −45° C. and during stirring gradual addition of 1.0 ml t-butyl acetate follows maintaining the temperature of the reaction mixture at −45° C. Stirring is continued 10 minutes, then 1.0 g methyl 5-(4-(4-fluorophenyl)-6-isopropyl-2-[methyl(methylsulfonyl)amino]pyrimidine-5-yl)-3(S)-hydroxypent-4(E)-enoate (Compound of Example 9) is added. Stirring is continued for 20 minutes and the reaction mixture is poured into 20 ml 5% phosphoric acid. 10 ml of t-butyl methyl ether are added and the product is extracted into organic phase. Organic phase is washed with 2×10 ml demi water. The solvents of the organic phase are evaporated off at reduced pressure at 60° C. 1.1 g of the light-brown syrupy mass of 3-deoxy-3-oxo-rosuvastatin t-butyl ester is produced and used without purification in the next step.

EXAMPLE 13

Rosuvastatin t-butyl Ester

Compound of Formula IX, where $R_6$=t-butyl 1.0 g t-Butyl 7-(4-(4-fluorophenyl)-6-isopropyl-2-[methyl (methylsulfonyl)amino]pyrimidine-5-yl)-5(S)-hydroxy-3-oxo-hept-6(E)-enoate (Compound of Example 12) is dissolved in 6 ml THF and 1 ml methanol under nitrogen. The solution is cooled to −80° C. and 1.0 ml of a 50% solution of methoxydiethylborane in THF is added. The reaction mixture is cooled to −95° C. and 0.15 g sodium borohydride is added in portions over 2 hours. The reaction mixture is maintained between −90° C. and 85° C. for 3.5 hours and 9 hours at room temperature. 0.3 ml of acetic acid is added and the mixture is concentrated by evaporation under reduced pressure. To the residue 3.0 ml of methanol are added and the solvents are distilled off under reduced pressure. The oily residue is dissolved in 10 ml of ethyl acetate and the resulting solution is washed with 3 ml demi water. The organic phase is concentrated by evaporation under reduced pressure at 70° C. yielding 0.95 g of the product.

EXAMPLE 14

Rosuvastatin Calcium 60.0 g rosuvastatin t-butyl ester (Compound of Example 13) and 21.0 ml 8M NaOH in 120 ml THF and 300 ml demi water are stirred at 50° C. for 2 hours whereupon the mixture is cooled to room temperature and washed twice with 540 ml of methylcyclohexane. Aqueous phase is evaporated at 60° C. under reduced pressure to 220 ml of total volume to eliminate organic solvents. The residue is rediluted with degassed demi-water to 440 ml of total volume. To the resulting solution 1.0 g of charcoal is added and the suspension is stirred half an hour. Aqueous solution of calcium chloride is added to the filtrate during stirring on ice-bath. The suspension formed is treated vigorously with ultraturrax at cca 18000 rpm for 3 minutes. The precipitate is filtered off, suspended in 100 ml demi water and treated again with ultraturrax at 18000 rpm for 3 minutes on ice-bath. The product is separated by filtration, washed with 30 ml ice-cold degassed demi-water, collected from the filter and dried 12 hours at 50° C. in vacuum desiccator. Yield: 25.05 g of rosuvastatin calcium (99.75% area, HPLC).

Alternatively the Title Compound is Prepared as Follows:

7.2 g t-butyl ester of rosuvastatin (Compound of Example 13) and 4.5 ml i-$PrNH_2$ in 35 ml demi-water are stirred in the autoclave at 98-100° C. for 2 hours. The solution formed is then cooled to room temperature and a very little amount of solid impurities is filtered off. Filtrate is washed 2×20 ml i-PrOAc and the water phase is then evaporated under reduced pressure at 70° C. and 15 mbar to remove solvents and i-propylamine. 7.15 g of white solid residue of rosuvastatin i-propylammonium salt is collected. This amount is added to 70 ml acetonitrile and the suspension formed is heated under reflux (80° C.) for 1 h. Then, it is being held for 2 h at 0° C. Subsequently, the product is separated by filtration. Yield: 6.7 g of white crystals of the pure product (>99.9% area, HPLC). 2.0 g of above rosuvastatin i-propylammonium salt, 13 ml demi-water and 2.0 ml 1 M calcium acetate are vigorously treated with ultraturax 2 minutes at 10000 rpm under nitrogen and then stirred 10 minutes with magnetic bar at 10° C. White precipitate is filtered off and washed with 2 ml demi-water. It is dried 1 hour on the filter and 2 hours at 50-60° C. and at 10 mbars. Yield: 1.67 g of rosuvastatin calcium (>99.8% area, HPLC, <0.1% sodium calculated on the content of calcium)

EXAMPLE 15

5-(trifluoroacetyloxy)methyl-4-(4-fluorophenyl)-6-isopropyl-2-[methyl(methylsulfonyl)amino]pyrimidine Compound of Formula II, where X=OCOCF$_3$ 21 g 5-hydroxymethyl-4-(4-fluorophenyl)-6-isopropyl-2-[methyl(methylsulfonyl)amino]pyrimidine (Compound of Formula I) and 13.2 ml of N-ethyl-diisopropylamine in 120 ml dichloromethane are stirred on ice bath, and thereto 10.2 ml of trifluoroacetyl anhydride are added during 5 minutes. Reaction mixture is stirred for another hour at room temperature whereupon the reaction mixture is washed twice by 120 ml of water, and after evaporation of organic phase under reduced pressure at 50° C., 27 mg of product are obtained.

EXAMPLE 16

5-(methanesulfonyl)methyl-4-(4-fluorophenyl)-6-isopropyl-2-[methyl(methylsulfonyl)amino]pyrimidine Compound of Formula II, where X=OSO$_2$CH$_2$ 3.5 g 5-hydroxymethyl-4-(4-fluorophenyl)-6-isopropyl-2-[methyl(methylsulfonyl)amino]pyrimidine (Compound of Formula I) and 2.2 ml of N-ethyl-diisopropylamine in 20 ml dichloromethane are stirred on ice bath, and while stirring thereto 2.0 g of methanesulfonyl anhydride are added. Reaction mixture is stirred for another 2 h at room temperature whereupon the reaction mixture is washed with 20 ml 1% phosphoric acid and 20 ml of water, and after evaporation of organic phase under reduced pressure at 50° C., 4.3 mg of product are obtained, which is crystallized from mixture of isopropyl acetate and hexane.

EXAMPLE 17

({4-(4-fluorophenyl)-6-isopropyl-2-[methyl(methylsulfonyl)amino]-5-pyrimidinyl}methyl)(tributyl) phosphonium trifluoroacetate (Compound of Formula III, where R$_1$=R$_2$=R$_3$=Bu, A=OCOCF$_3$)

24 g 5-(trifluoroacetyloxy)methyl-4-(4-fluorophenyl)-6-isopropyl-2-[methyl(methylsulfonyl)amino]pyrimidine (Compound of Example 16) and 16.0 ml of tributylphosphine are stirred in 110 ml of chlorobenzene for 1 hour at 120-125° C. Thereafter the reaction mixture is cooled to room temperature and thereto 160 ml ether is added. A precipitate forms which is washed with ether and dried under vacuum. 30.5 g product is obtained.

EXAMPLE 18

({4-(4-fluorophenyl)-6-isopropyl-2-[methyl(methylsulfonyl)amino]-5-pyrimidinyl}methyl)(tributyl) phosphonium trifluoroacetate (Compound of Formula III, where R$_1$=R=R$_3$=Bu, A=OCOCF$_3$)

2.0 g 5-(trifluoroacetyloxy)methyl-4-(4-fluorophenyl)-6-isopropyl-2-[methyl(methylsulfonyl)amino]pyrimidine (Compound of Example 15) and 1.24 g of triphenylphosphine are stirred in 8 ml of chlorobenzene for 4 h at 120-125° C. Solvent is evaporated at 60° C. and the product is obtained as a clear waxy substance in 3.3 yield, which crystallizes from isopropyl acetate.

EXAMPLE 19

({4-(4-fluorophenyl)-6-isopropyl-2-[methyl(methylsulfonyl)amino]-5-pyrimidinyl}methyl)(trifenyl) phosphonium mesylate (Compound of Formula III, where R$_1$=R=R$_3$=Ph. A=OSO$_2$CH$_3$)

0.86 g 5-(methansulfonyl)methyl-4-(4-fluorophenyl)-6-isopropyl-2-[methyl(methylsulfonyl)amino]pyrimidine (Compound of Example 16) and 0.60 ml of tributylphosphine are stirred in 5 ml isopropyl acetate for ½ h at 80° C. Reaction mixture is cooled and 0.5 ml n-hexane is added. Upon cooling to room temperature a precipitate forms, which is washed with ether and dried to yield 1.1 g product which is poorly soluble in tetrahydrofurane.

EXAMPLE 20

({4-(4-fluorophenyl)-6-isopropyl-2-[methyl(methylsulfonyl)amino]-5-pyrimidinyl}methylphosphonium trifluoroacetate (Compound of Formula III, where A=CF$_3$COO)

56.55 g 5-(4-(4-fluorophenyl)-6-isopropyl-2-[methyl(methylsulfonyl)amino]pyrimidine-5-yl)methanol (160 mmol), 26.8 ml triethylamine (192 mmol) is mixed with 200 ml of n-butyl acetate and 23.4 ml trifluoroacetanhydride (168 mmol) is added dropwise to the reaction mixture at room temperature. After finishing of the addition the reaction mixture is warmed to 60° C. and all components are dissolved, then tri-n-butylphosphine (44.8 ml, 176 mmol) is added. The mixture is heated under reflux for 2 h, then cooled and washed twice with 400 ml of water. The second aqueous crop is rewashed with 100 ml of n-butyl acetate. Collected organic phases are concentrated by evaporation to 150 ml, cooled to 20° C. and while stirring 400 ml of methyl t-butyl ether is added. After 8 h of stirring the product is collected by filtration, washed twice with 400 ml of methyl t-butyl ether and dried 4 h at 70° C. and 50 mBar. Yield 94.0 g (90%).

EXAMPLE 21

Methyl 5-(4-(4-fluorophenyl)-6-isopropyl-2-[methyl (methylsulfonyl)amino]pyrimidine-5-yl)-3(S)-t-butyldimethyisilyloxy-pent-4(E)-enoate (Compound of Formula V, where R$_5$=Me, R$_4$=t-butyldimethylsilyl)

Solution of 10 g of ((4-(4-fluorophenyl)-6-isopropyl-2-(N-methylmethylsulfonamido) pyrimidin-5-yl)methyl)tripropylphosphonium trifluoroacetate in 62 ml of THF is cooled to −30° C. and then 8.5 ml of 2 M solution of sodium bis(trimethylsilyl)amide is added. After 10 min. reaction mixture is cooled to −40° C. and 9 g of methyl 3-(tert-butyldimethylsilyloxy)-4-oxobutanoate is added. Reaction is quenched after 5 minutes with 8 ml of acetic acid. 155 ml of heptane is added, organic phase is washed 3 times with 77 ml of water. Then the crude product is isolated by evaporation. Crude product is dissolved in 10 ml of mixture ethyl acetate/heptane 2:3 and filtered through 50 g of silica gel and the product is isolated by evaporation. Yield: 10.8 g of yellow oil.

EXAMPLE 22

α,α-Dimethylphenethyl 7-(4-(4-fluorophenyl)-6-isopropyl-2-[methyl(methylsulfonyl)-amino]pyrimidine-5-yl)-5(S)-t-butyldimethysilyloxy-3-oxo-hept-6(E)-enoate 89.8 ml of 1.8 M lithium di-iso-propylamide (LDA) in THF/heptane/ethylbenzene is diluted with 63 ml THF, cooled to −65° C., followed by the gradual addition 41.2 ml 4 M of α,α-dimethylphenethyl acetate solution in THF during stirring. The temperature of the reaction mixture is maintained between −60 and −70° C. for 40 minutes. Then, the solution of 21.1 g methyl 5-(4-(4-fluorophenyl)-6-isopropyl-2-[methyl(methylsulfonyl)amino]-pyrimidine-5-yl)-3(S)-t-butyldimethylsilyloxy-pent-4(E)-enoate in 63 ml THF is added gradually during stirring. After the addition, the temperature is kept between −60 and −70° C. for 2 hours during stirring. To the stirring reaction mixture is then added 53 ml of 50% aq. acetic acid and the temperature is allowed to rise to 20° C. and the reaction mixture is kept stirred for 2 hours. The two layers formed are separated and the upper organic layer is washed twice with 60 ml 10% solution of NaCl. The solvents of the organic phase are evaporated off at reduced pressure at 60° C. yielding 55.4 g of crude product containing redundant α,α-dimethylphenethyl acetate. $MH^+=726$.

EXAMPLE 23

α,α-Dimethylphenethyl 7-(4-(4-fluorophenyl)-6-isopropyl-2-[methyl(methylsulfonyl)-amino]pyrimidine-5-yl)-5(S)-hydroxy-3-oxo-hept-6(E)-enoate 40.0 g α,α-dimethylphenethyl 7-(4-(4-fluorophenyl)-6-isopropyl-2-[methyl(methyl-sulfonyl)-amino]pyrimidine-5-yl)-5(S)-t-butyldimethylsilyloxy-3-oxo-hept-6(E)-enoate and 15 ml triethylamine trihydrofluoride in 120 ml t-butanol and 5 ml water are stirred together at 50° C. 4 hours. Solvents are removed by evaporation at 60° C. under reduced pressure. The oily residue is dissolved in 200 ml toluene and washed with 2×150 ml 2% aq. NaCl. Toluene phase is evaporated at 60° C. under reduced pressure leaving behind 32 g of the crude oily product. $MH^+=612$.

EXAMPLE 24

Methyl 5-(4-(4-fluorophenyl)-6-isopropyl-2-[methyl (methylsulfonyl)amino]-pyrimidine-5-yl)-3(S)-tetrahydropyran-2'-yl-oxy-pent-4(E)-enoate 41.0 g methyl 5-(4-(4-fluorophenyl)-6-isopropyl-2-[methyl(methylsulfonyl)amino]-pyrimidine-5-yl)-3(S)-hydroxy-pent-4(E)-enoate, 9.5 ml 3,4-dihydro-2H-pyrane, 0.5 g (−)-camphorsulfonic acid in 41 ml dichloromethane are stirred for 6 hours at room temperature under nitrogen atmosphere. Then, the reaction mixture is washed twice with 50 ml of water and the organic phase is evaporated at reduced pressure at 60° C. yielding 49.90 g of the product. $MH^+=536$.

EXAMPLE 25

(1R)-(−)-menthyl 7-(4-(4-fluorophenyl)-6-isopropyl-2-[methyl-(methylsulfonyl)amino]-pyrimidine-5-yl)-5(S)-tetrahydropyran-(2')-yl-oxy-3-oxo-hept-6(E)-enoate 42.0 ml of 1.8 M LDA in THF/heptane/ethylbenzene is diluted with 25 ml THF, cooled to −65° C., followed by the gradual addition of 16.5 ml (−)-menthyl acetate solution during stirring. The temperature of the reaction mixture is maintained between −60 and −70° C. for 30 minutes. Then, the solution of 10.0 g 5-(4-(4-fluorophenyl)-6-isopropyl-2-[methyl(methylsulfonyl)-amino]pyrimidine-5-yl)-3(S)-tetrahydropyran-2'-yl-oxy-pent-4(E)-enoate in 63 ml THF is added gradually during stirring. After the addition, the temperature is kept between −45 and −55° C. for 1.5 hours during stirring. To the stirring reaction mixture is then added 60 ml of 50% aq. acetic acid and the temperature is raised to 20° C. and the reaction mixture is kept stirred for 2 hours. The two layers formed are separated and the upper organic layer is washed twice with 100 ml 10% solution of NaCl. The solvents of the organic phase are evaporated off at reduced pressure at 60° C. yielding 26.7 g of crude product containing redundant menthyl acetate. $MH^+=702$.

EXAMPLE 26

(1R)-(−)-Menthyl 7-(4-(4-fluorophenyl)-6-isopropyl-2-[methyl(methylsulfonyl)amino]-pyrimidine-5-yl)-5(S)-hydroxy-3-oxo-hept-6(E)-enoate 26.7 g (−)-Menthyl 7-(4-(4-fluorophenyl)-6-isopropyl-2-[methyl(methylsulfonyl)-amino]pyrimidine-5-yl)-5(S)-tetrahydropyran-(2')-yl-oxy-3-oxo-hept-6(E)-enoate, 4.6 g sulfamic acid, 53 ml methanol and 5.3 ml water are mixed together and the resulting reaction mixture is stirred at 55° C. for 3 hours. The reaction mixture is cooled to room temperature, diluted with 60 ml of water and extracted twice with the mixture of 80 ml of heptane and 20 ml i-propyl acetate. Combined organic extracts are washed with 140 ml of 10% aq. NaCl. The solvents of the organic phase are evaporated at reduced pressure at 60° C. yielding 23.2 g of the crude product containing redundant menthyl acetate. $MH^+=618$.

EXAMPLE 27

α,α-Dimethylphenethyl 7-(4-(4-fluorophenyl)-6-isopropyl-2-[methyl(methylsulfonyl)amino]pyrimidine-5-yl)-5(S)-hydroxy-3-oxo-hept-6(E)-enoate 38 ml of 1.8 M LDA in THF/heptane/ethylbenzene+16 ml THF is diluted with 16 ml THF, cooled to −65° C., followed by the gradual addition of 17.8 ml 4 M α,α-dimethylphenethyl acetate during stirring. The temperature of the reaction mixture is maintained between −60 and −70° C. for 30 minutes. In the meantime, 8.0 g methyl 5-(4-(4-fluorophenyl)-6-isopropyl-2-[methyl(methylsulfonyl)amino]-pyrimidine-5-yl)-3(S)-hydroxy-pent-4(E)enoate is dissolved in 28 ml THF at RT and the resulting solution is cooled to −30 to −40° C. followed by the addition of 1 M t-butylmagnesium chloride. The reaction mixture is then stirred 30 minutes at the same temperature. Then, the second solution is added to the first one all at once and the temperature of the reaction mixture is maintained between −50 to −60° C. for 1.5 h. To the stirred reaction mixture is added 50 ml 50% aq. acetic acid and the temperature is allowed to rise to 20° C. and the reaction mixture is kept stirring for 8 hours at the same temperature. The two layers formed are separated and the upper organic layer is washed twice with 40 ml 10% solution of NaCl. The solvents of the organic phase are evaporated off at reduced pressure at 60° C. yielding 20.5 g of crude product containing redundant α,α-dimethylphenethyl acetate. HPLC shows 90% area of consumption of the starting material and 75% area of the product. The product is used as such in the next step without further purification. $MH^+$=612.

EXAMPLE 28

Rosuvastatin (1R)-(−)-menthyl Ester 23.2 g (1R)-(−)-Menthyl 7-(4-(4-fluorophenyl)-6-isopropyl-2-[methyl-(methylsulfonyl)amino]-pyrimidine-5-yl)-5(S)-hydroxy-3-oxo-hept-6(E)-enoate is dissolved in the mixture of 64 ml methanol and 236 ml THF followed by cooling to −80° C. 10.75 ml of the solution of 4 M diethylmethoxyborane in THF is added. After 15 minutes 2.9 g of sodium borohydride is added. Stirring is continued for 4 hours at −80° C. followed by the addition of 32 ml of glacial acetic acid. The temperature is raised to 20° C. and stirring is continued for another 2 hours. Then, 345 ml of ethyl acetate is added and reaction mixture is washed with 645 ml of 5% $NaHCO_3$. Aqueous phase is reextracted with 215 ml of ethyl acetate and combined organic phases are washed with 200 ml of 10% NaCl. Organic phase is separated off, dried with 21 g anh. $MgSO_4$, filtered and evaporated at 60° C. under reduced pressure yielding 22.5 of the crude product. $MH^+$=620.

EXAMPLE 29

Rosuvastatin α,α-dimethylphenethyl Ester

The 20.5 g crude α,α-dimethylphenethyl 7-(4-(4-fluorophenyl)-6-isopropyl-2-[methyl-(methylsulfonyl)amino]pyrimidine-5-yl)-5(S)-hydroxy-3-oxo-hept-6(E)-enoate from previous experiment is dissolved in 185 ml MeOH/THF (1:4=vol.:vol.) and the resulting solution is cooled to −80° C. The solution of 5.5 ml 50% methoxydiethylborane in THF is added during stirring and the reaction mixture is stirred 20 minutes under nitrogen at −80° C. Then, 1.2 g of sodium borhydride is added and the stirring is continued for 4 hours at the same temperature. The reaction mixture is quenched with 22 ml of glacial acetic acid and the volatile materials are evaporated under reduced pressure at 50° C. 150 ml of ethyl acetate are added to the residue and the resulting suspension is washed 3×100 ml of the saturated aq. $NaHCO_3$. The organic layer is separated and evaporated at reduced pressure at 60° C. yielding 19.2 g of the crude oily product.

A small portion of the product was purified through the column of silica (mobile phase: ethyl acetate/heptane=1:1) getting analytical sample.

MS (EI): $MH^+$=614

$^1$H-NMR: ($CDCl_3$) 1.27 (6H, d), 1.48 (7H, m), 2.39 (1H, m), 2.41 (1H, dd), 3.38 (1H, hept), 3.53 (3H, s), 3.58 (3H, s), 3.76 (1H, m), 4.15 (1H, m), 4.45 (1H, m), 5.45 (1H, dd, $J_1$=16 Hz), 6.64 (1H, dd, $J_1$=16 Hz), 7.05-7.33 (7H, m), 7.63-7.69 (2H, m).

Conversion into Rosuvastatin:

To 22.5 g of the crude rosuvastatin α,α-dimethylphenethyl ester are added 30 ml of THF, 60 ml of water and 12 ml 8 M NaOH. The reaction mixture is stirred 3 hours at 50° C. The hydrolysis is monitored by quantitative HPLC analysis, which shows after the completion of reaction 53% overall yield from starting methyl 5-(4-(4-fluorophenyl)-6-isopropyl-2-[methyl(methylsulfonyl)amino]-pyrimidine-5-yl)-3(S)-hydroxy-pent-4(E)-enoate.

EXAMPLE 30

Methyl(3-(4-fluorophenyl)-1-isopropyl-1H-indol-2-yl)-3(S)-t-butyldimethylsilyloxy-pent-4(E)-enoate (Compound of Formula V, where $R_5R$=Me, R=t-butyldimethylsilyl)

Solution of 8.9 g of (3-(4-fluorophenyl)-1-isopropyl-1H-indol-2-yl)methyl)tributyl-phosphonium trifluoroacetate in 62 ml of THF is cooled to −30° C. and then 8.5 ml of 2 M solution of sodium bis(trimethylsilyl)amide is added. After 10 min. reaction mixture is cooled to −50° C. and 9 g of methyl 3-(tert-butyldimethylsilyloxy)-4-oxobutanoate is added. Reaction is quenched after 5 minutes with 8 ml of acetic acid. 150 ml of heptane is added, and organic phase is washed 3 times with 80 ml of water. Then the crude product is isolated by evaporation. Crude product is dissolved in 10 ml of mobile phase (ethyl acetate/heptane 2:3) and filtered through 50 g of silica gel, washed with mobile phase and the product is isolated by evaporation. Yield: 9.2 g of brown oil.

The product could be converted to methyl(3-(4-fluorophenyl)-1-isopropyl-1H-indol-2-yl)-3(S)-t-butyldimethylsilyloxy-pentanoate by catalytic hydrogenation in the presence of palladium on charcoal.

The invention claimed is:

1. A process for preparation of compound of following formula:

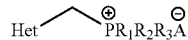

which comprises treating a compound of following formula:

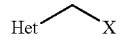

wherein X is a leaving group with one or more phosphines of Formula X

wherein

Het is a residue of the following formula;

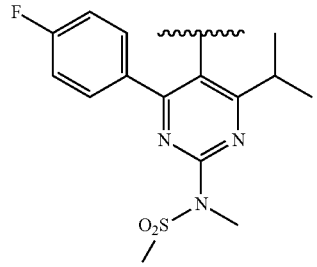

A is an anion of a strong organic acid, selected from the group consisting of mesyloxy, fluoroacetyloxy, and trifluoroacetyloxy;

R₁, R₂, R₃, are the same or different and are selected from substituted (by halo, alkyl or aryl) or unsubstituted $C_1$-$C_{12}$ alkyl or $C_3$-$C_6$ cycloalkyl or $C_1$-$C_8$ alkenyl or $C_5$-$C_6$ cycloalkenyl or $C_5$-$C_{10}$ aryl; and X is a leaving group selected from the group consisting of mesyloxy, fluoroacetyloxy, and trifluoroacetyloxy.

2. A process for preparation of compound of Formula III:

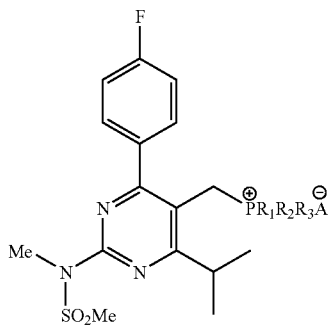

wherein R₁, R₂, and R₃ are ethyl or

R₁, R₂, and R₃ are n-butyl or

R₁, R₂, and R₃ are methyl or

R₁ and R₂ are phenyl, and R₃ is methyl or

R₁ is phenyl, and R₂ and R₃ are methyl, and

A is selected from the group consisting of mesylate, fluoroacetate, and trifluoroacetate;

which comprises treating a compound of Formula II:

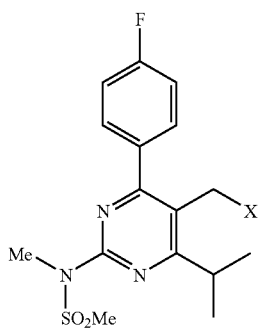

wherein X is a member selected from the group consisting of a mesyloxy, a fluoroacetyloxy, and a trifluoroacetyloxy, with phosphines of Formula X:

PR₁R₂R₃ wherein R₁, R₂ and R₃ are as defined above in a solvent or a mixture of solvents at temperatures between 0° C. and 80° C.

3. The process of claim 2, wherein a solvent is THF or $C_1$-$C_4$ alkyl acetate or toluene or $C_1$-$C_4$ alcohol.

4. The process of claim 3, wherein a solvent is ethyl acetate.

5. A process for preparing a compound Formula II:

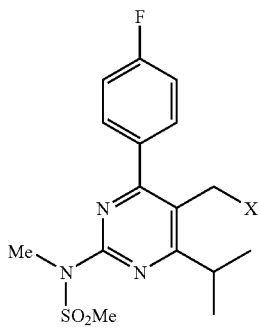

wherein X is bromine which comprises halogenation of a compound of formula:

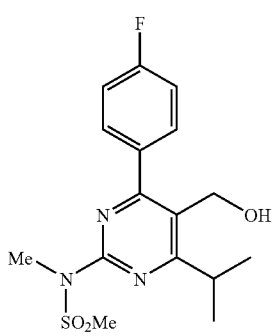 [SMILES: CC(C)c1nc(N(C)S(C)(=O)=O)nc(-c2ccc(F)cc2)c1CO]

with an aqueous solution of concentrated hydrobromic acid, having an acid concentration of at least 47%, at temperatures between 30° C. and 100° C.

6. The process of claim 5, wherein the concentration of aqueous solution of hydrobromic acid is at least 62%.

7. The process of claim 6, wherein a weight ratio between 62% water solution of hydrobromic acid and a compound of formula

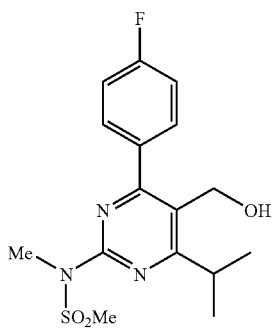 [SMILES: CC(C)c1nc(N(C)S(C)(=O)=O)nc(-c2ccc(F)cc2)c1CO]

is between 3 and 30 at temperatures between 40° C.-100° C.

8. The process according to claim 5, further comprising the steps of:

a) optionally neutralizing a hydrohalogenic acid;

b) extracting a compound Formula II, wherein X is a bromo group, with an aprotic organic solvent immiscible in water;

c) optionally washing the organic solvent solution with water or with a buffer solution in aqueous media in a pH range between 5 and 14.

9. The process of claim 8, wherein the organic solvent is a compound selected from the group consisting of toluene, ethyl acetate, dichloromethane, and mixtures thereof.

10. The process of claim 9, comprising subsequent isolation of a solid compound Formula II, wherein X is bromo, by evaporation of the solvent at reduced pressure.

11. A process for preparing a compound of Formula II

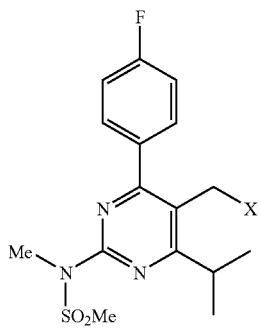

wherein X is selected from the group consisting of an alkanoyloxy, arenecarboxy, alkanesulphonyloxy and arenesulphonyloxy;

which comprises esterification of a compound of formula

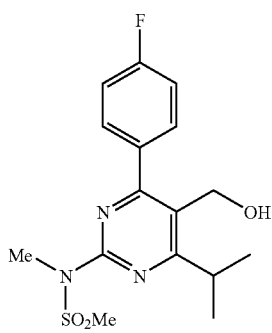 [SMILES: CC(C)c1nc(N(C)S(C)(=O)=O)nc(-c2ccc(F)cc2)c1CO]

with corresponding acid or its derivative selected from acid halide or anhydride.

12. A process according to claim 11 wherein X is trifluoroacetyloxy and esterification is performed with trifluoroacetic acid anhydride, at temperatures between 30° C. and 150° C.

13. The process of claim 11, wherein compound of Formula II is subsequently used without isolation.

14. A process for manufacturing a compound of Formula III:

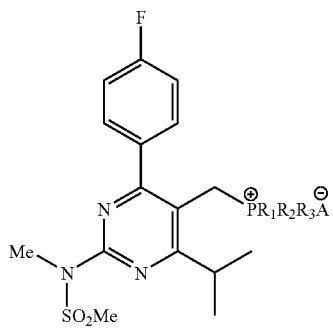

where $R_1$, $R_2$, and $R_3$ are independently selected from alkyl, or aryl and A is trifluoroacetate, reacting Formula I:

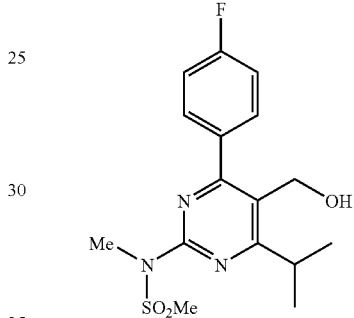

with trifluoroacetic acid and subsequently without isolation with triaryl phosphine or mixed alkyl aryl phosphine or trialkyl phosphine.

15. A compound of Formula III:

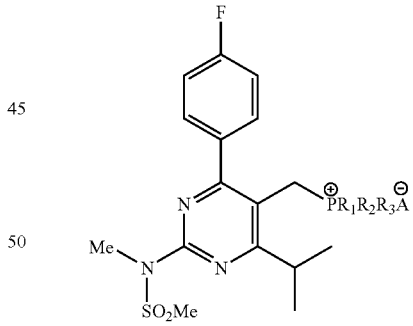

wherein A is trifluoroacetate, fluoroacetate or mesylate; and wherein $R_1$, $R_2$, and $R_3$ are ethyl or $R_1$, $R_2$, and $R_3$ are n-butyl or $R_1$, $R_2$, and $R_3$ are methyl or $R_1$ and $R_2$ are phenyl, and $R_3$ is methyl or $R_1$ is phenyl, and $R_2$ and $R_3$ are methyl.

16. A compound of claim 15 where A is trifluoroacetate and $R_1$, $R_2$, and $R_3$ are n-butyl.

* * * * *